(12) United States Patent
Zack et al.

(10) Patent No.: US 9,382,229 B2
(45) Date of Patent: Jul. 5, 2016

(54) COMPOUNDS AND METHODS OF USE THEREOF FOR TREATING NEURODEGENERATIVE DISORDERS

(75) Inventors: Donald J. Zack, Baltimore, MD (US); Cynthia Berlinicke, Baltimore, MD (US); Laszlo Hackler, Zagrab (HU); Zhiyong Yang, Baltimore, MD (US); Joseph P. Steiner, Mount Airy, MD (US); Tomas Vojkovsky, Palm Beach Gardens, FL (US); Dana Ferraris, Eldersburg, MD (US); Barbara S. Slusher, Baltimore, MD (US); James Inglese, Bethesda, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 13/985,702

(22) PCT Filed: Feb. 15, 2012

(86) PCT No.: PCT/US2012/025228
§ 371 (c)(1),
(2), (4) Date: Feb. 20, 2014

(87) PCT Pub. No.: WO2012/112674
PCT Pub. Date: Aug. 23, 2012

(65) Prior Publication Data
US 2014/0187540 A1    Jul. 3, 2014

Related U.S. Application Data

(60) Provisional application No. 61/443,035, filed on Feb. 15, 2011.

(51) Int. Cl.
*C07D 403/12*    (2006.01)
*C07D 401/14*    (2006.01)
*C07D 403/14*    (2006.01)
*C07D 453/02*    (2006.01)

(52) U.S. Cl.
CPC ............ *C07D 403/12* (2013.01); *C07D 401/14* (2013.01); *C07D 403/14* (2013.01); *C07D 453/02* (2013.01)

(58) Field of Classification Search
CPC .. C07D 401/14; C07D 403/14; C07D 403/12; A61K 31/506
USPC ........................................................ 544/295
See application file for complete search history.

(56) References Cited

U.S. PATENT DOCUMENTS

2006/0106027 A1    5/2006   Furet et al.
2010/0130501 A1    5/2010   Li et al.

FOREIGN PATENT DOCUMENTS

| WO | WO 2004000833 A1 * | 12/2003 |
| WO | 2007/056164 A2 | 5/2007 |
| WO | 2007/056221 A2 | 5/2007 |
| WO | WO 2008115973 A2 * | 9/2008 |
| WO | 2010/017541 A2 | 2/2010 |
| WO | 2011/050192 A1 | 4/2011 |
| WO | 2011/119777 A2 | 9/2011 |

OTHER PUBLICATIONS

J.H. Poupaert, Drug Design: Basic Principles and Applications, in 2 Encyclopedia of Pharmaceutical Technology 1362-1369, 1367 (James Swarbrick ed., 3rd ed., 2007).*
E. Kwong et al., 412 International Journal of Pharmaceutics, 1-7 (2011).*
V.I. Minkin et al., The Tautomerism of Heterocycles: Five-membered Rings with Two or More Heteroatoms, in 76 Advances in Heterocyclic Chemistry 157-323, 160-162 (Alan R. Katritzky et al., eds., 2000).*
D. Bebbington et al., 19 Bioorganic & Medicinal Chemistry Letters, 3586-3592 (2009).*
S.M. Guichard et al., 44 European Journal of Cancer, 310-317 (2008).*

* cited by examiner

*Primary Examiner* — Alexander R Pagano
(74) *Attorney, Agent, or Firm* — Ward and Smith, P.A.; Jeffrey W. Childers; David A. Fazzolare

(57) ABSTRACT

Compounds, compositions, kits and methods for treating conditions related to neurodegeneration or ocular disease, are disclosed.

2 Claims, 10 Drawing Sheets

| Sample Name | CurveClass | AC50 (uM) | Efficacy |
|---|---|---|---|
| LESTAURTINIB | 1.2 | 0.7467 | 52.2927 |
| NCGC00188382-01 | 1.3 | 0.4199 | 80.6033 |
| VX-680/MK-0457 | 2.1 | 2.1045 | 343.901 |
| SUNITINIB MALATE | 2.1 | 1.7155 | 180.4111 |

*Fig. 8B*

COMPOUNDS AND METHODS OF USE THEREOF FOR TREATING NEURODEGENERATIVE DISORDERS

CROSS-REFERENCE TO RELATED APPLICATIONS

This application is a 35 U.S.C. §317 U.S. national phase entry of International Application No. PCT/US2012/025228 having an international filing date of Feb. 15, 2012, which claims the benefit of U.S. Provisional Application No. 61/443,035, filed Feb. 15, 2011, the content of which is herein incorporated by reference in its entirety.

FEDERALLY SPONSORED RESEARCH OR DEVELOPMENT

This invention was made with government support under 5R21EY019737-02 awarded by the National Institutes of Health. The government has certain rights in the invention.

BACKGROUND

Neurodegenerative disorders afflict numerous patients throughout the world and can be devastating to patients and caregivers. Such disorders also can result in great financial burdens, with annual costs currently exceeding several hundred billion dollars in the United States alone. Current treatments for such disorders often are inadequate. Further, many such disorders are age-related, and thus their incidence is rapidly increasing as demographics trend toward an aging population. For example, glaucoma, a disease, disorder, or condition that results in damage to the optic nerve, is a major cause of vision loss and blindness, especially in the elderly. Although various treatments for glaucoma exist, many such treatments are of limited efficacy and/or have significant side effects. Reduction of intraocular pressure, generally through pharmacologic or surgical intervention, is presently the mainstay of glaucoma therapy. Such therapies, however, often are only partially effective and generally cannot restore neuronal cell function once such function has been lost.

SUMMARY

In some aspects, the presently disclosed subject matter provides a compound of Formula (Ia):

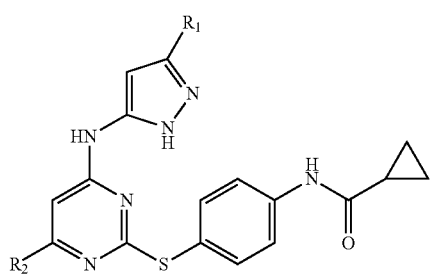

wherein:
$R_1$ is substituted or unsubstituted alkyl;
$R_2$ is selected from the group consisting of halogen and a heterocyclic group selected from the group consisting of 4-(pyrrolidin-1-yl)piperidinyl, piperidin-4-ol, and 1,4-diazepanyl; and pharmaceutically acceptable salts thereof.

In other aspects, the presently disclosed subject matter provides a method for treating or preventing a neurodegenerative disease, disorder, or condition in a subject in need thereof, the method comprising administering to the subject a therapeutically effective amount of a compound of Formula (I), or a pharmaceutically acceptable salt thereof, thereby treating or preventing the neurodegenerative disease, disorder, or condition:

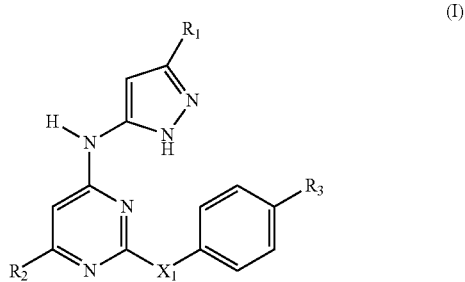

wherein:
$X_1$ is S or O;
$R_1$ is selected from the group consisting of H, substituted or unsubstituted alkyl, and substituted or unsubstituted cycloalkyl;
$R_2$ is selected from the group consisting of halogen, substituted or unsubstituted cycloalkyl or heterocycloalkyl; $-NR_4(CH_2)_n-NR_5R_6$, wherein n is an integer from 1 to 8 and $R_4$, $R_5$, and $R_6$ are each independently $C_1$-$C_4$ alkyl, wherein $R_5$ and $R_6$ together can form a substituted or unsubstituted cycloalkyl or heterocycloalkyl; and $-NR_7R_8$, wherein $R_7$ and $R_8$ are each independently H, $C_1$-$C_4$ alkyl, or heterocycloalkyl;
$R_3$ is selected from the group consisting of H or $NR_9-C(=O)-R_{10}$, wherein $R_9$ is H or $C_1$-$C_4$ alkyl and $R_{10}$ is substituted or unsubstituted $C_1$-$C_3$ alkyl; and pharmaceutically acceptable salts thereof.

In particular aspects, the neurodegenerative disease, disorder, or condition is an ocular-related neurodegeneration, such as glaucoma.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
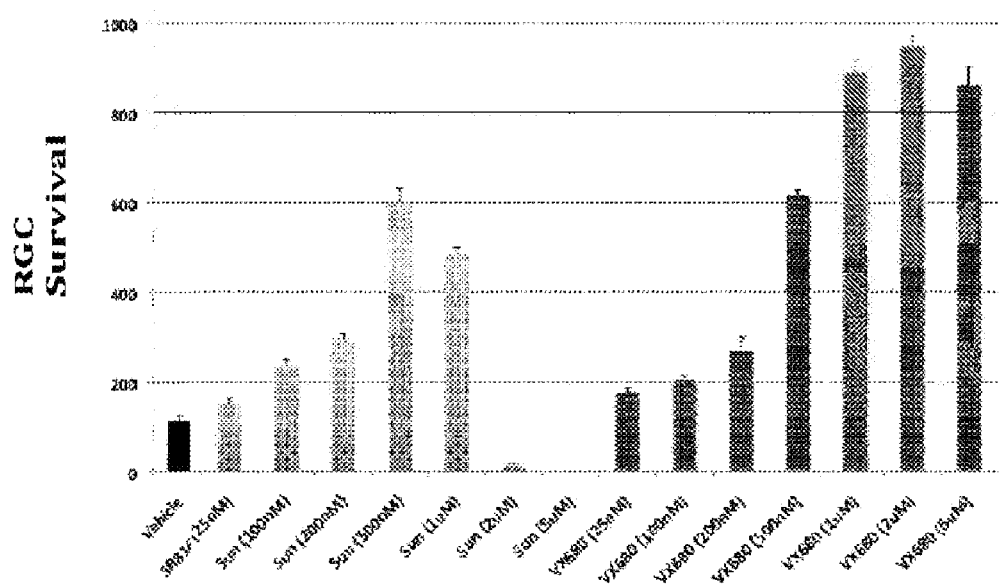
Figure 2:
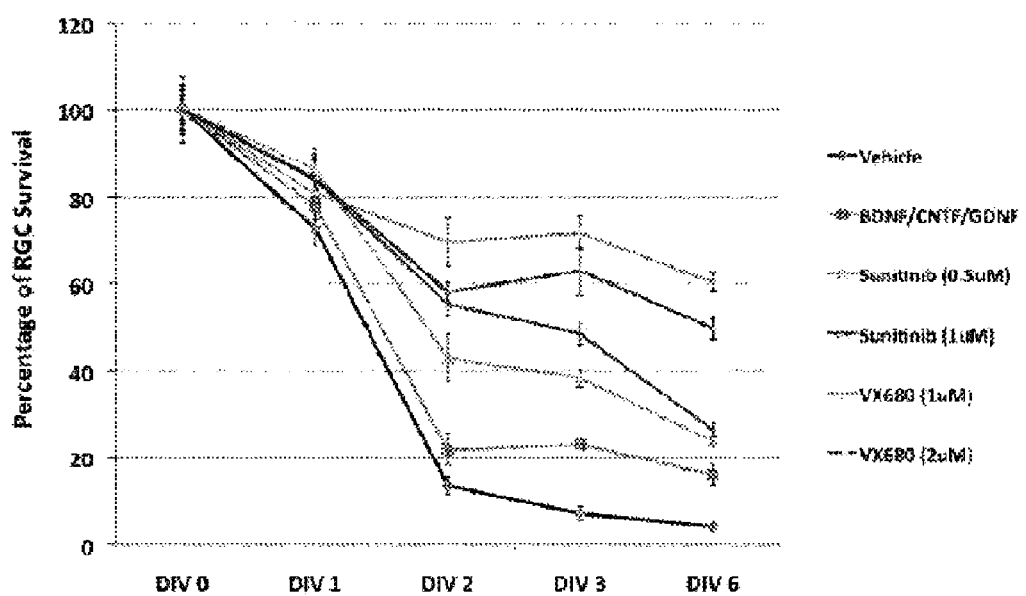
Figure 3:
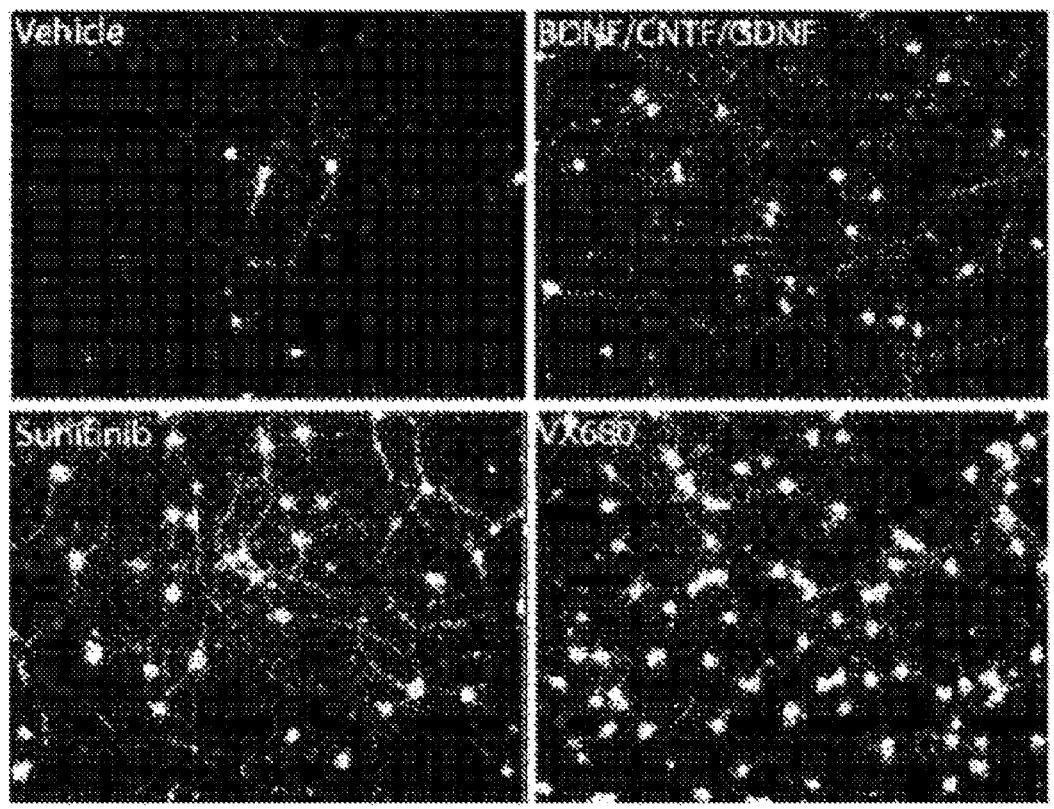
Figure 4:
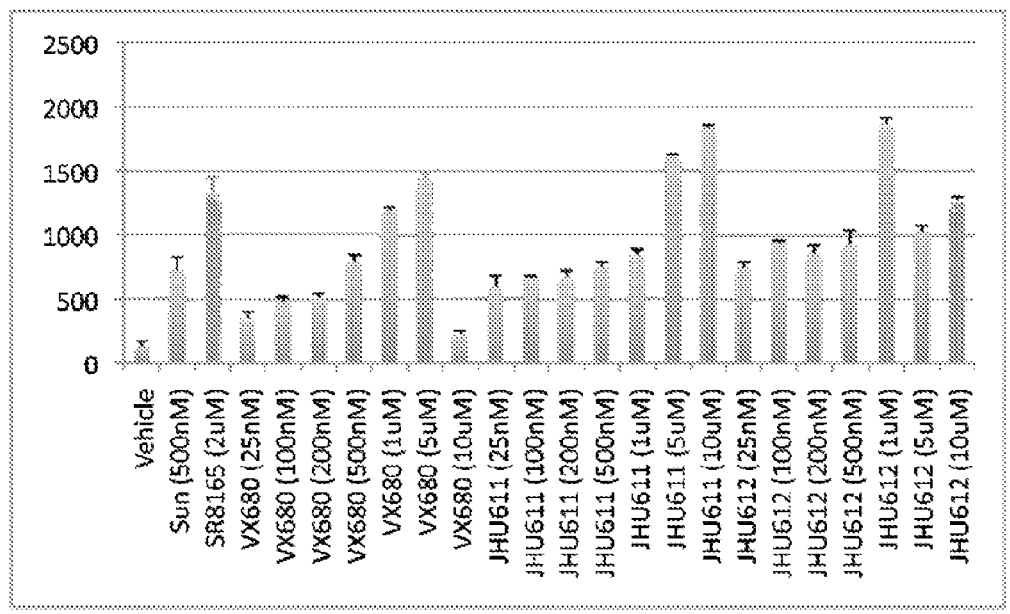
Figure 5:
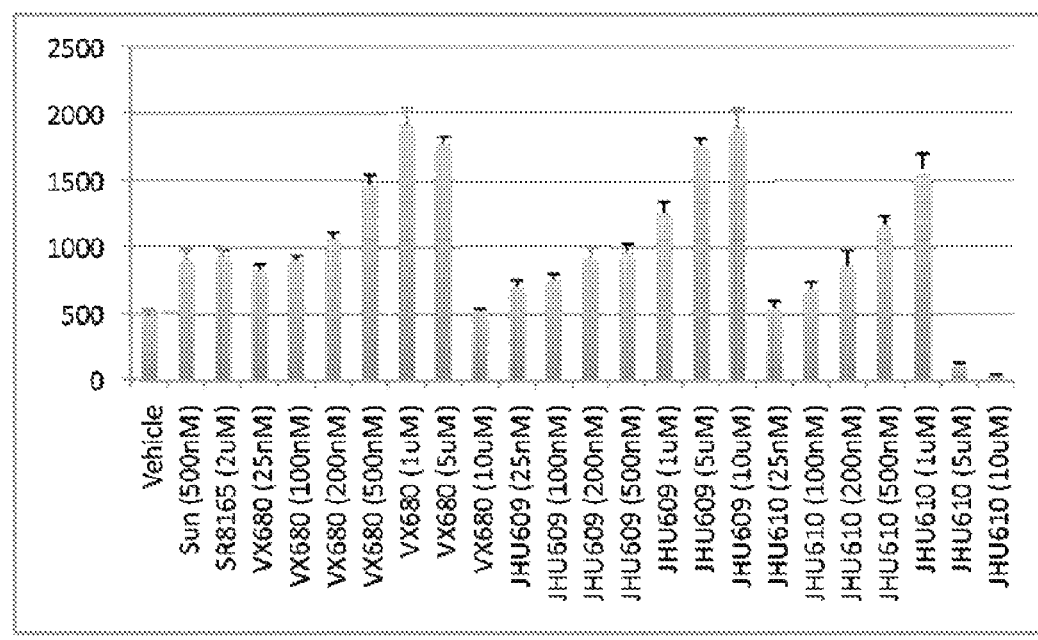
Figure 6:
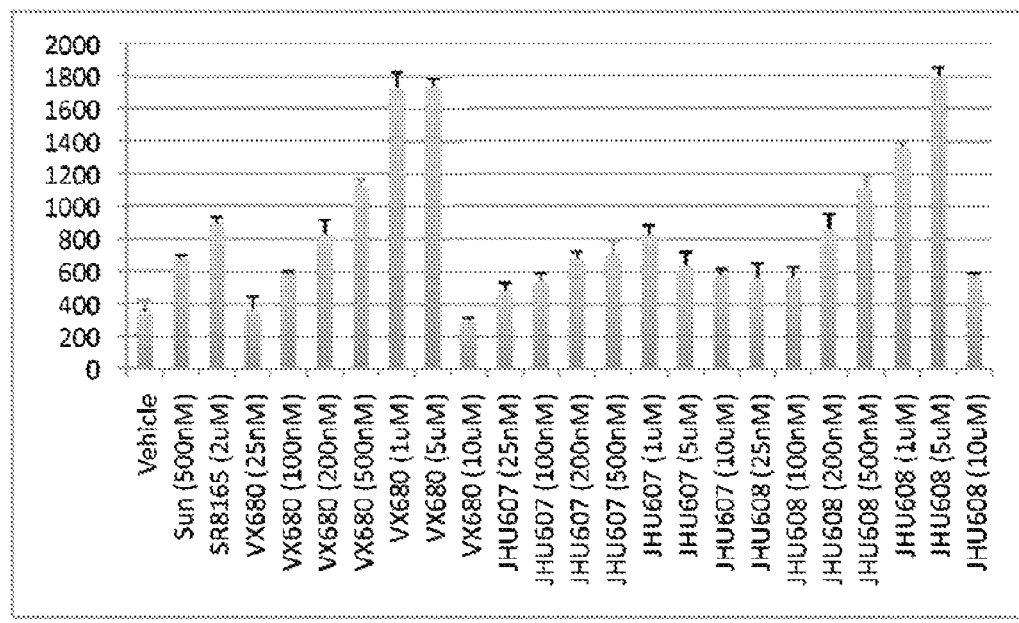
Figure 7:
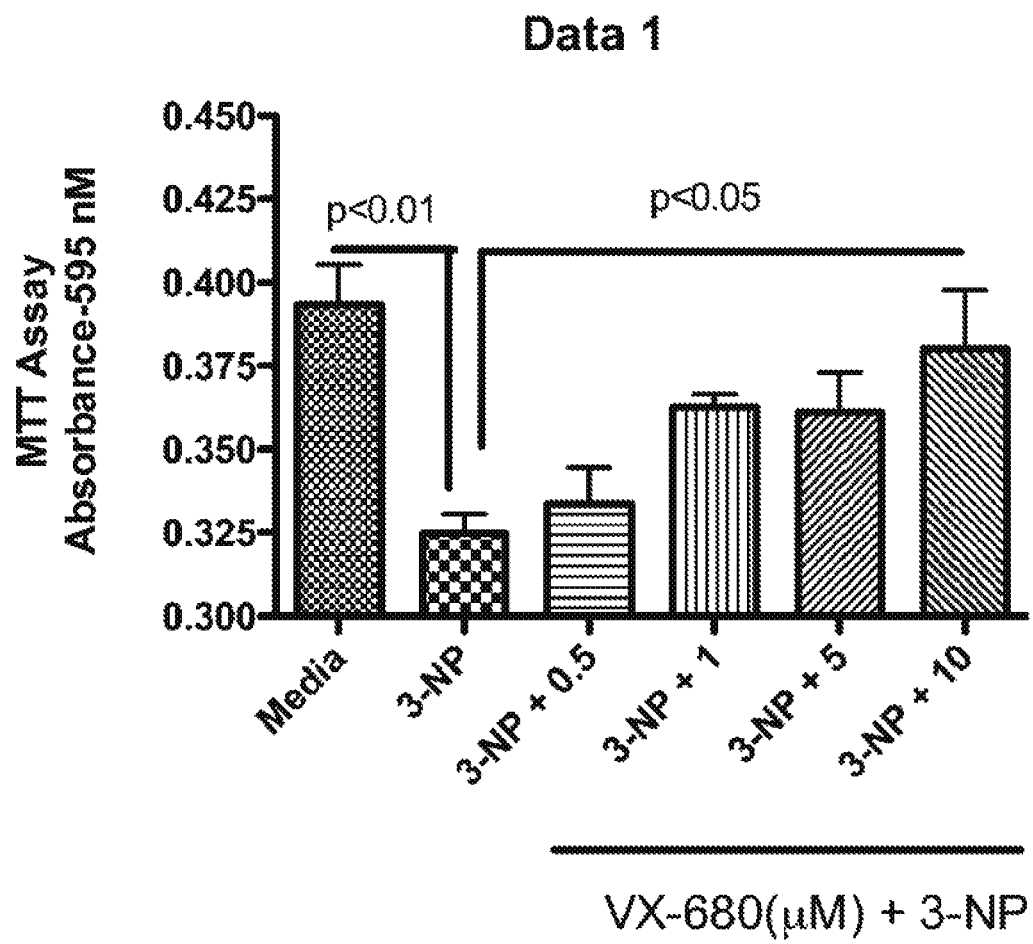
Figure 8A:
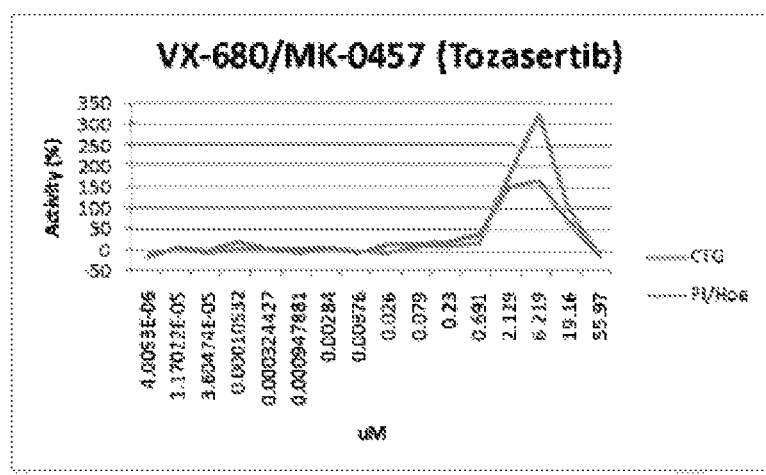
Figure 8C:
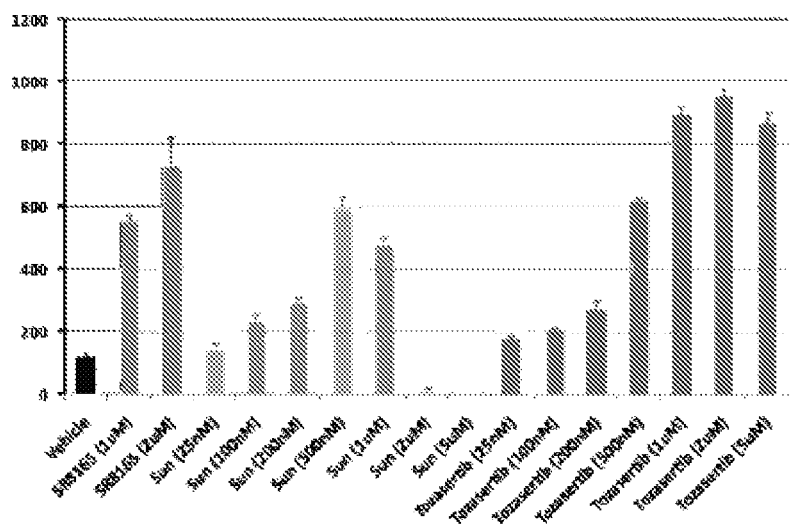

Having thus described the presently disclosed subject matter in general terms, reference will now be made to the accompanying Figures, which are not necessarily drawn to scale, and wherein:

FIG. 1 demonstrates that VX680 promotes retinal ganglion cell (RGC) survival in vitro. RGCs were purified from 2-5 day-old C57BL/6 mice, and cultured for 3 days in a media containing Neurobasal and B27, with or without 25-5000 nM of sunitinib (sun) or VX680. RGC survival was determined by combined staining with Calcein A M, Hoescht, and Ethidium homodimer. Images were acquired and analyzed with a Cellomics imager. Error bars: Mean±S.E.M.;

FIG. 2 is a comparison of the relative efficacy of sunitinib, VX680 and neurotrophic factors in promoting RGC survival in vitro. FIG. 2 shows RGC survival with and without various compounds after various days in culture. Purified mouse RGCs were cultured in the presence of sunitinib (0.5 or 1 μM), VX680 (1 or 2 μM), and a combination of BDNF, CNTF, and GDNF, for up to 6 days. RGC survival (percent survival compared to zero time) was determined at the indicated day in vitro (DIV) (0, 1, 2, 3, and 6 DIV). Error bars: Mean±S.E.M.;

FIG. 3 is representative images showing the RGCs from the study described in FIG. 2;

FIG. 4 shows that VX680 analogs JHU611 and JHU612 promote RGC survival. Purified mouse RGCs were cultured in the presence of sunitinib (0.5 μM), 25-5000 nM of VX680, JHU611 or JHU612, for 3 days. RGC survival was determined by combined staining with Calcein A M, Hoescht, and Ethidium homodimer. Images were acquired and analyzed with a Cellomics imager. Error bars: Mean±S.E.M.;

FIG. 5 demonstrates that VX680 analogs JHU609 and JHU610 promote RGC survival. Purified mouse RGCs were cultured in the presence of sunitinib (0.5 μM), 25-5000 nM of VX680, JHU609 or JHU610, for 3 days. RGC survival was determined by combined staining with Calcein A M, Hoescht, and Ethidium homodimer. Images were acquired and analyzed with a Cellomics imager. Error bars: Mean±S.E.M.;

FIG. 6 demonstrates that VX680 analogs JHU607 and JHU608 promote RGC survival. Purified mouse RGCs were cultured in the presence of sunitinib (0.5 μM), 25-5000 nM of VX680, JHU607 or JHU608, for 3 days. The percentages of RGC survival was determined by combined staining with Calcein A M, Hoescht, and Ethidium homodimer. Images were acquired and analyzed with a Cellomics imager. Error bars: Mean±S.E.M.;

FIG. 7 demonstrates that VX680 promotes the survival of hippocampal neurons against mitochondrial injury and oxidative stress. Cell death of hippocampal neurons was induced by the mitochondrial toxin 3-nitropropionic acid (3-NP). VX680 was added to the media at concentrations of 0.5 μM, 1 μM, 5 μM and 10 μM. Cell survival was determined using a MTT assay. The effect of VX680 on cell survival was analyzed with the student t-test. Error bars: Mean±S.D.; and FIGS. 8A-8C demonstrate the identification of VX680 and NCGC00188382-01 as neuroprotective compounds through an RGC-based high content screen. Survival of purified mouse RGCs with increasing concentrations of VX680 (tozasertib) was determined by measuring cellular ATP levels with CellTiter-Glo (CTG), or by combined staining with Propidium iodide (PI) and Hoescht (Hoe) (PI/Hoe) (FIG. 8A). The efficacy in promoting primary mouse RGC survival by VX680 and NCGC00188382-01 was quantified and compared to sunitinib (FIGS. 8B and 8C).

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Compounds, Compositions, and Methods for Treating Neurodegenerative Disorders Glaucoma is a major cause of visual loss and blindness in elderly Americans and throughout the world. One approach for treating glaucoma and other optic nerve diseases, as well as other neurodegenerative diseases, disorders, or conditions is through neuroprotective agents that promote the survival of neurons or a portion thereof (e.g., the neuron cell body, an axon, or a dendrite).

It previously has been shown, that protein kinase inhibitors identified through a high content screen of libraries of small molecule compounds can promote the survival and/or neurite outgrowth of retinal ganglion cells (RGCs). See, for example, International PCT Patent Application Publication Nos., WO2010/017541, to Zack et al., published Feb. 11, 2010, and WO2011/119777 to Zack et al., published Sep. 29, 2011, each of which is incorporated by reference in their entirety. RGCs are cells in the retina that die in glaucoma and whose loss leads to vision loss. Accordingly, based on the activity of the presently disclosed compounds on RGCs, the presently disclosed compounds can by used for treating glaucoma and/or other optic nerve diseases. Further, based on their activity on other neurons, e.g., hippocampal cell cultures, the presently disclosed compounds can be used to treat other neurodegenerative diseases in which there is a decreased function and/or loss of neurons.

A. Compounds of Formula (I)

In some embodiments, the presently disclosed subject matter provides compound of Formula (Ia):

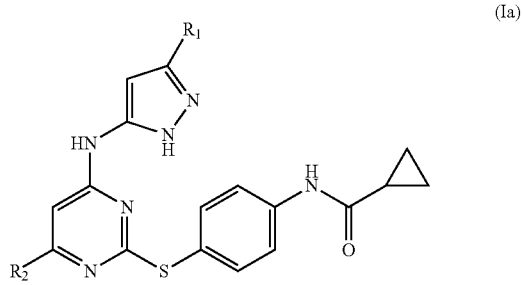

(Ia)

wherein:

$R_1$ is substituted or unsubstituted alkyl;

$R_2$ is selected from the group consisting of halogen and a heterocyclic group selected from the group consisting of 4-(pyrrolidin-1-yl)piperidinyl, piperidin-4-ol, and 1,4-diazepanyl; and pharmaceutically acceptable salts thereof.

In particular embodiments, the compound of Formula (Ia) is selected from the group consisting of:

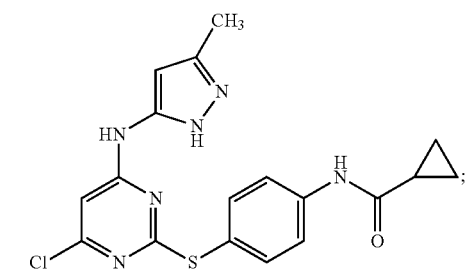

JHU-607

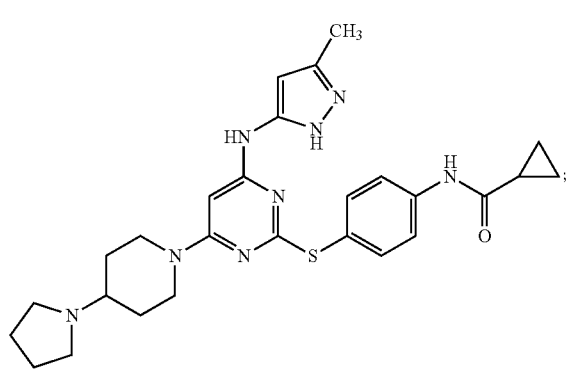

JHU-610

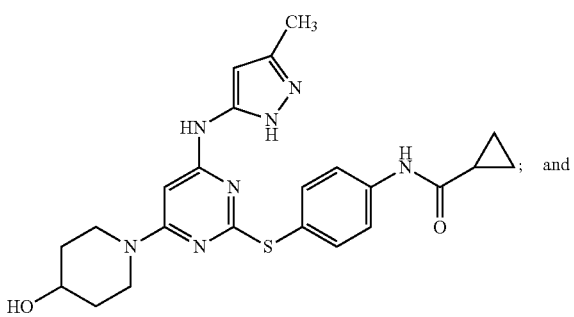

JHU-611; and

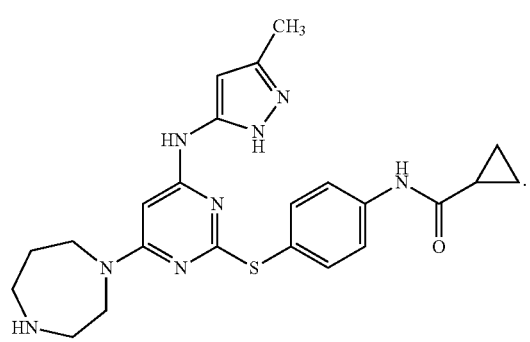

JHU-612 and pharmaceutically acceptable salts thereof.

B. Methods of Treatment

In other embodiments, the presently disclosed subject matter provides a method for treating or preventing a neurodegenerative disease, disorder, or condition in a subject in need thereof, the method comprising administering to the subject a therapeutically effective amount of a compound of Formula (I), or a pharmaceutically acceptable salt thereof, thereby treating or preventing the neurodegenerative disease, disorder, or condition:

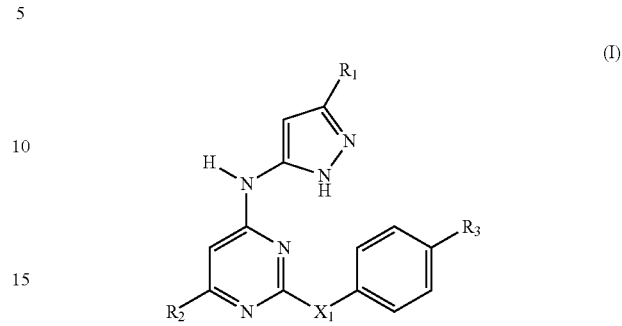

(I)

wherein:

$X_1$ is S or O; $R_1$ is selected from the group consisting of H, substituted or unsubstituted alkyl, and substituted or unsubstituted cycloalkyl; $R_2$ is selected from the group consisting of halogen, substituted or unsubstituted cycloalkyl or heterocycloalkyl; —$NR_4(CH_2)_n$—$NR_5R_6$, wherein n is an integer from 1 to 8 and $R_4$, $R_5$, and $R_6$ are each independently $C_1$-$C_4$ alkyl, wherein $R_5$ and $R_6$ together can form a substituted or unsubstituted cycloalkyl or heterocycloalkyl; and —$NR_7R_8$, wherein $R_7$ and $R_8$ are each independently H, $C_1$-$C_4$ alkyl, or heterocycloalkyl; $R_3$ is selected from the group consisting of H or $NR_9$—C(=O)—$R_{10}$, wherein $R_9$ is H or $C_1$-$C_4$ alkyl and $R_{10}$ is substituted or unsubstituted $C_1$-$C_3$ alkyl; and pharmaceutically acceptable salts thereof.

In particular embodiments, the compound of Formula (I) is selected from the group consisting of:

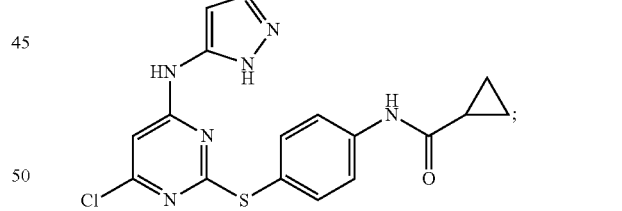

JHU-607

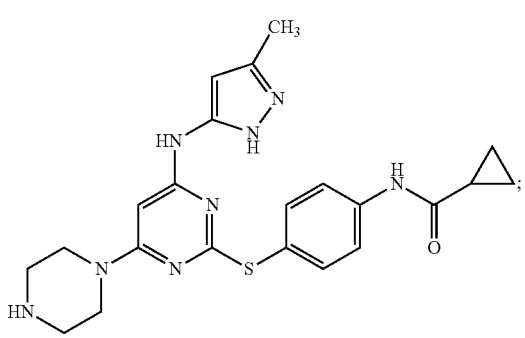

JHU-608

JHU-609
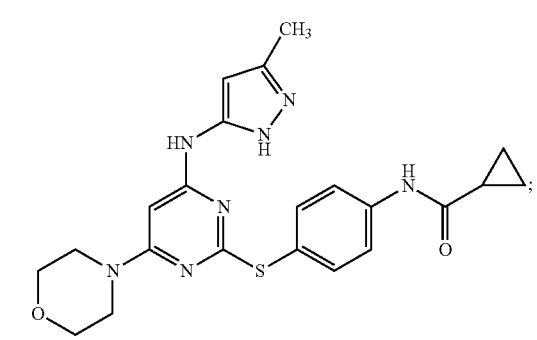

JHU-610
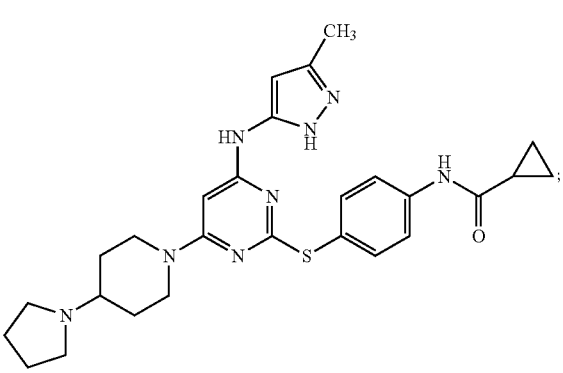

JHU-611
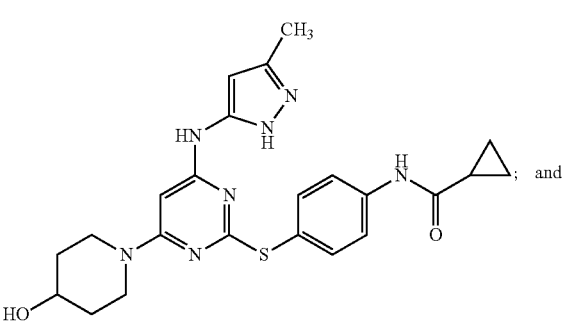

JHU-612
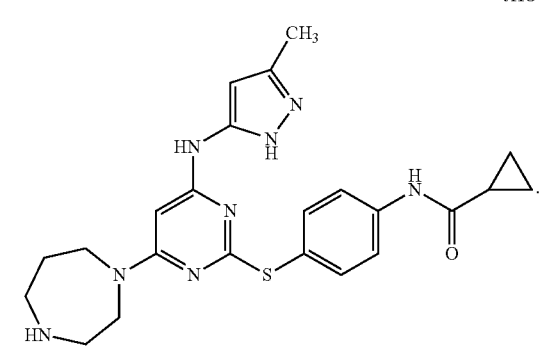

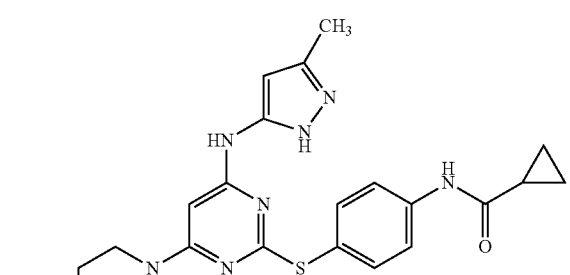

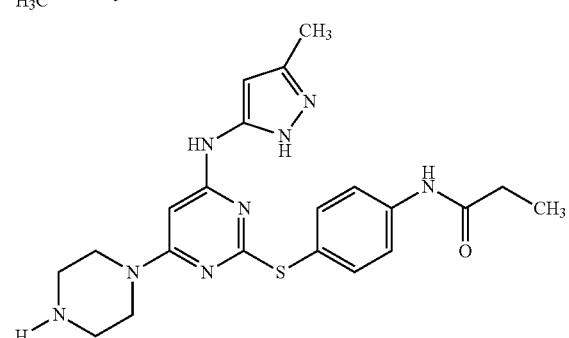

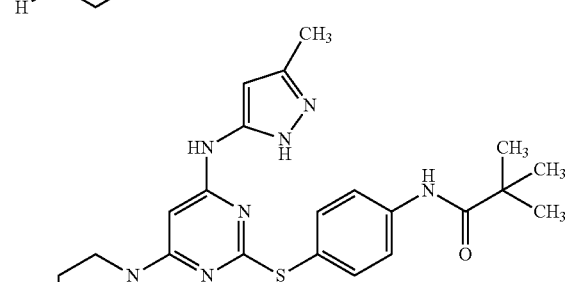

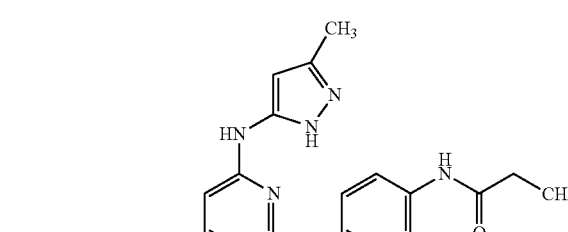

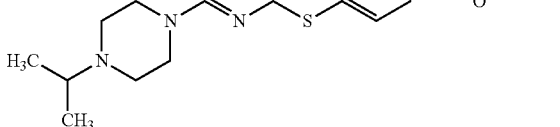

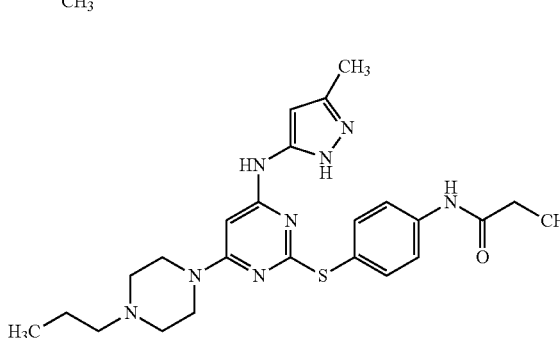

In further embodiments, the presently disclosed method includes a compound of Formula (I) selected from the group consisting of the following compounds disclosed in International PCT Patent Application Publication No. WO2004/000833, which is incorporated herein by reference in its entirety. Without wishing to be bound to any one particular theory, such compounds are believed to be protein kinase inhibitors.

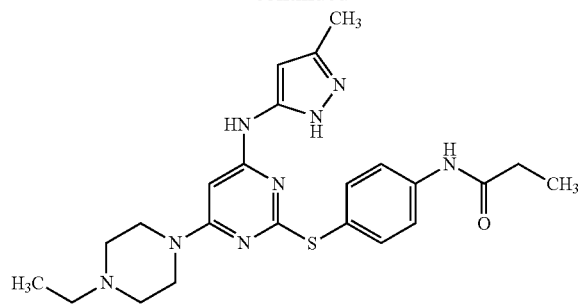
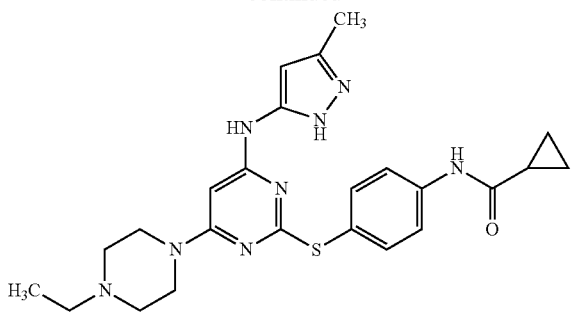
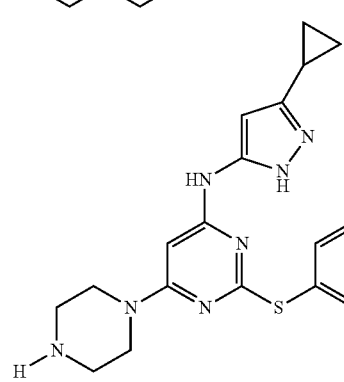
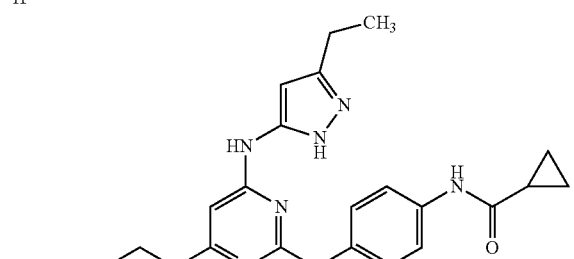
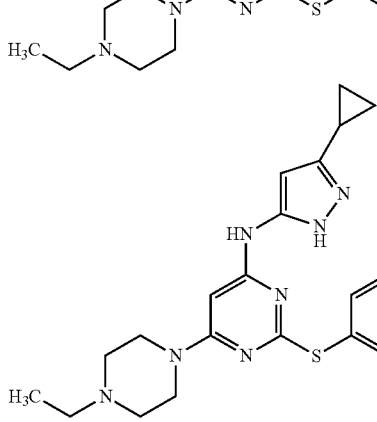
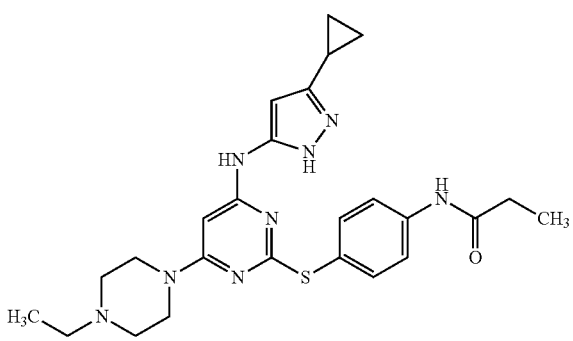

-continued
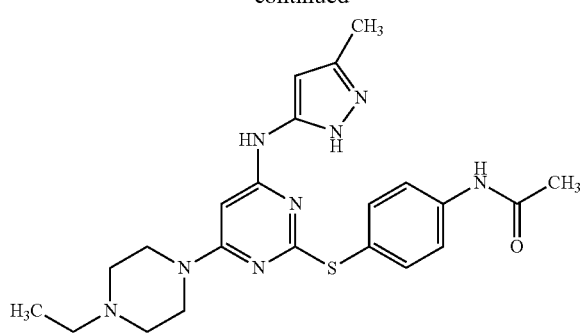
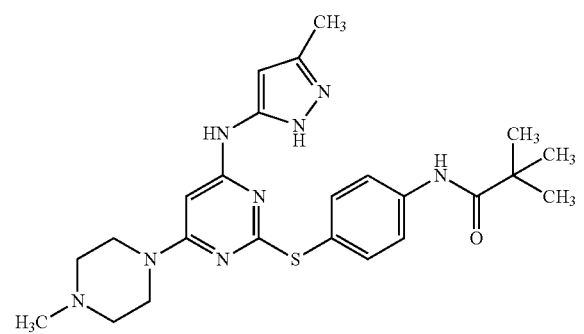
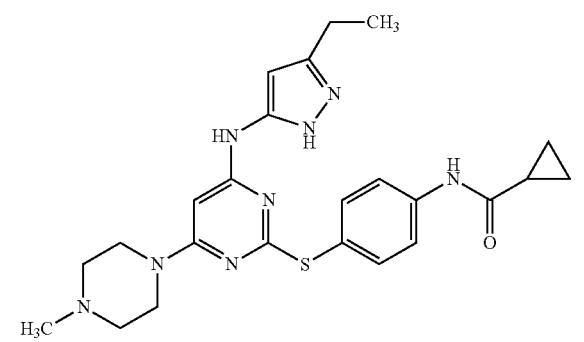
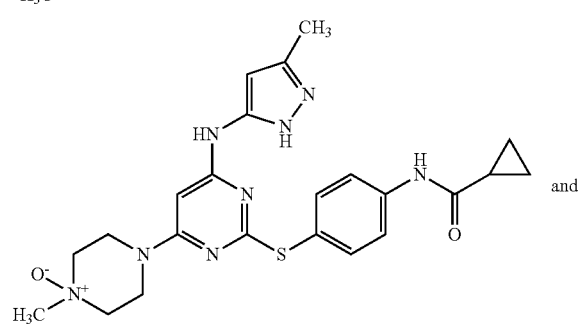
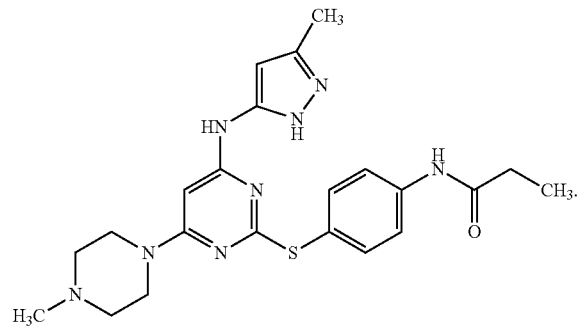
and
In other embodiments, the presently disclosed methods include a compound of Formula (I) selected from the group consisting of the following compounds also disclosed in WO2004/000833, and also believed to be protein kinase inhibitors.
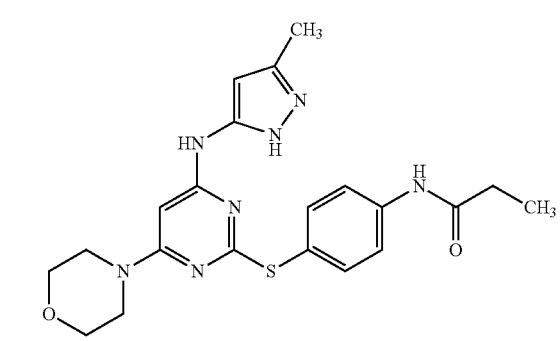
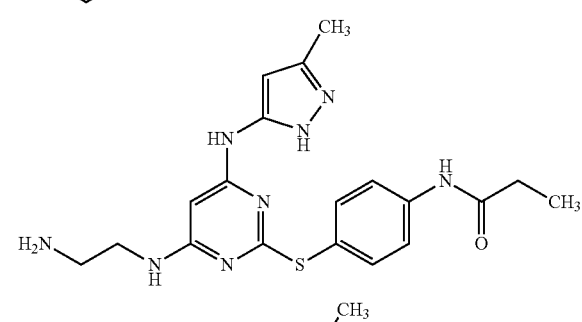
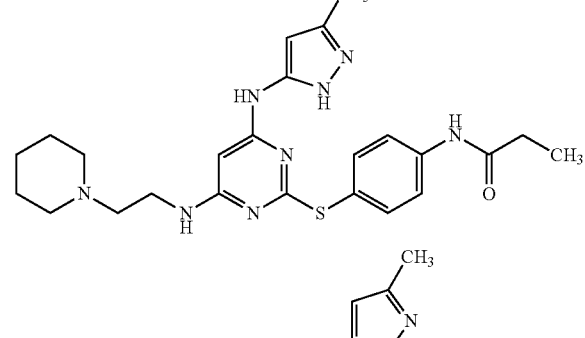
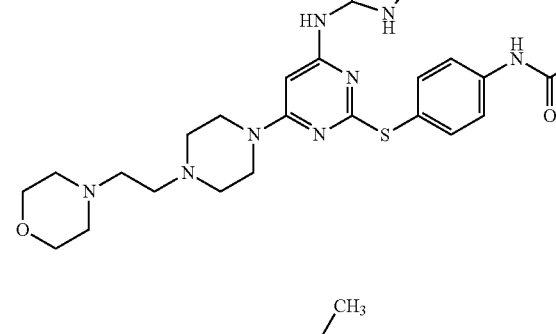
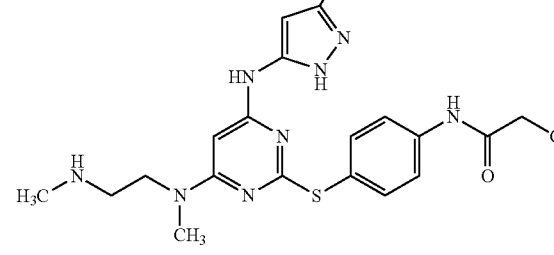

-continued
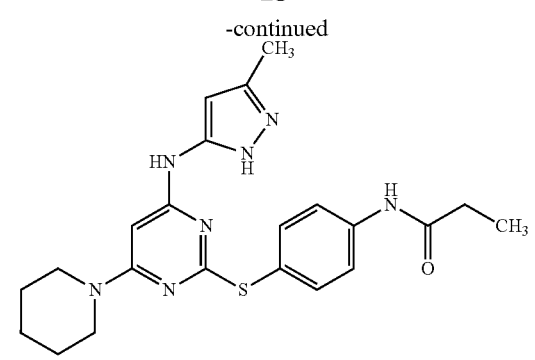
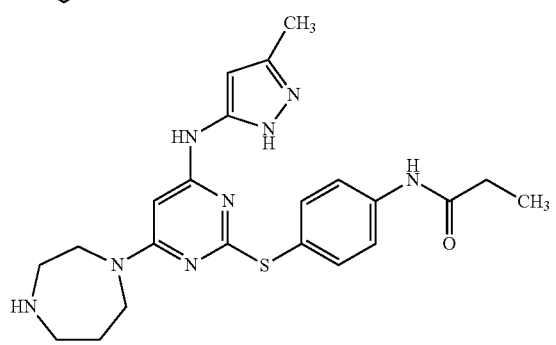
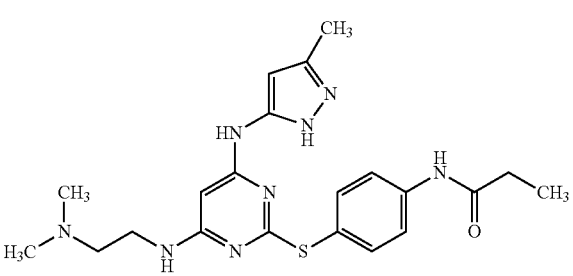
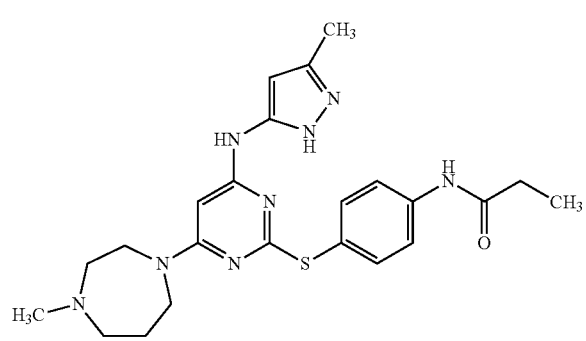
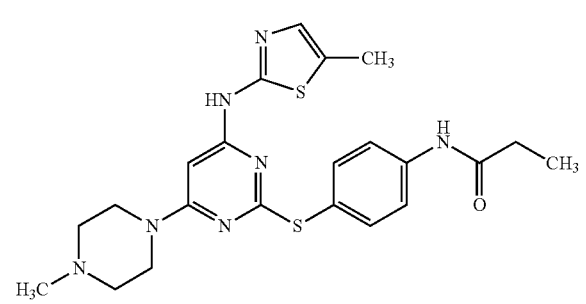
-continued
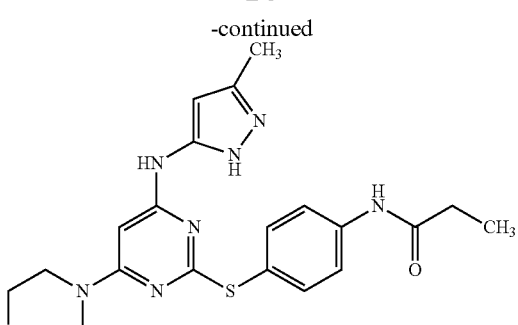
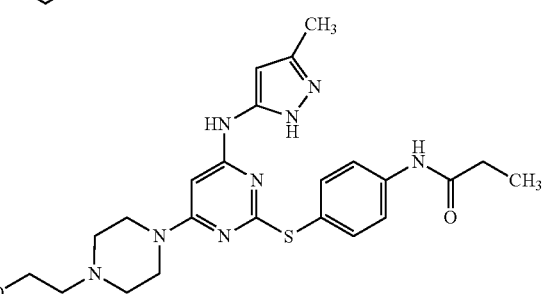
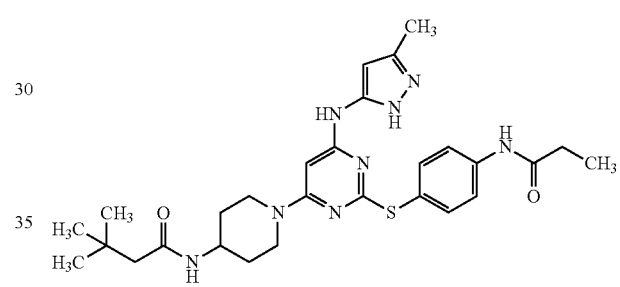
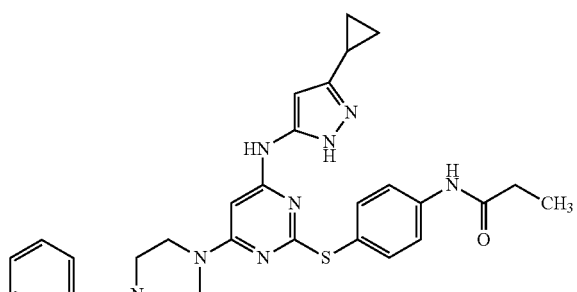
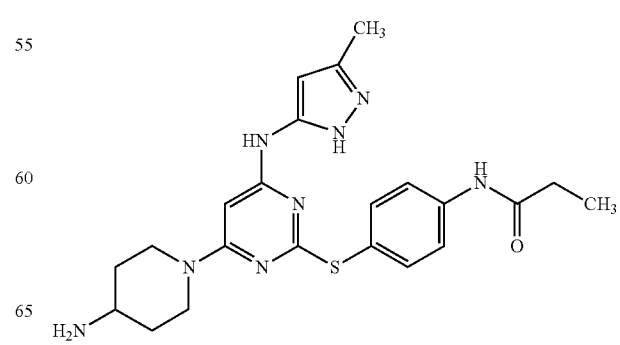

-continued
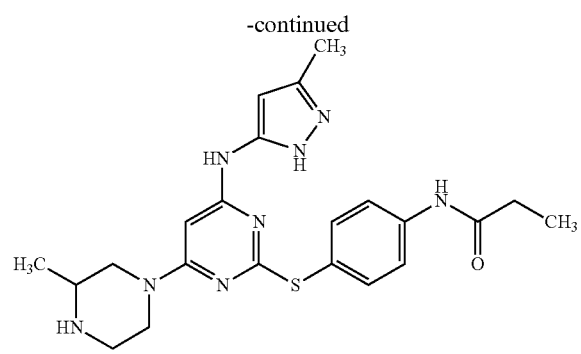
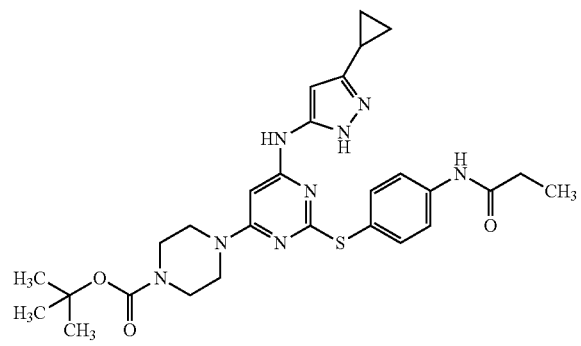
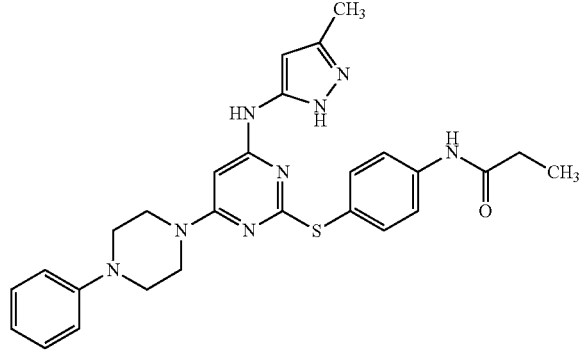
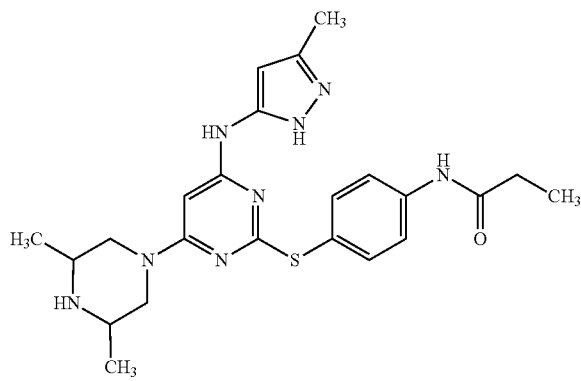
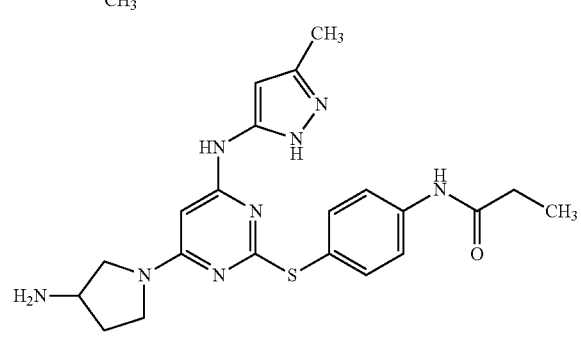
-continued
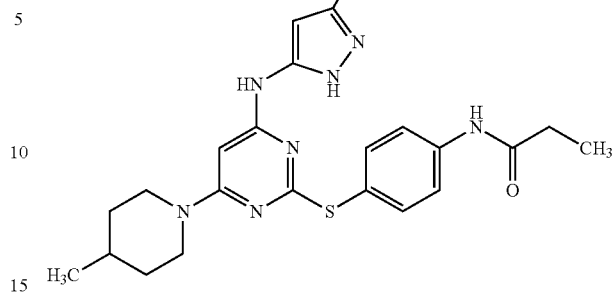
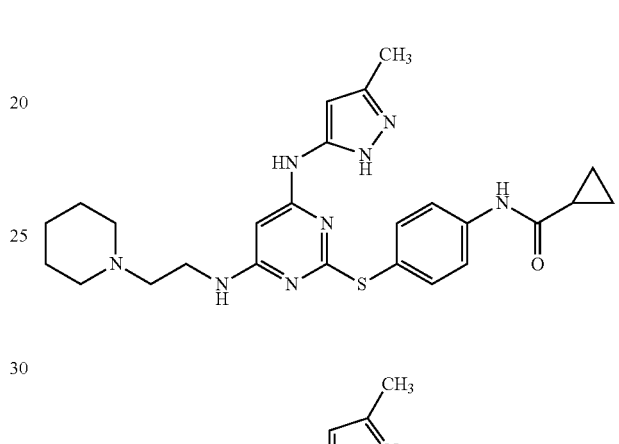
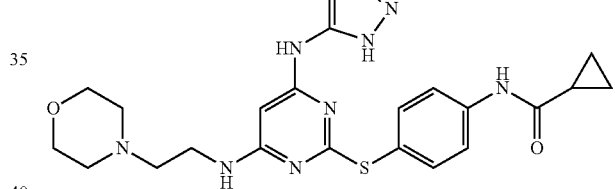
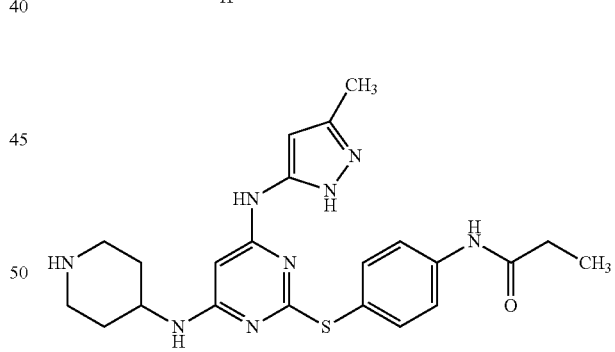
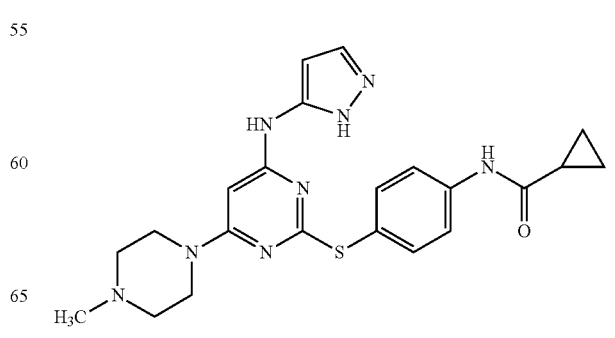

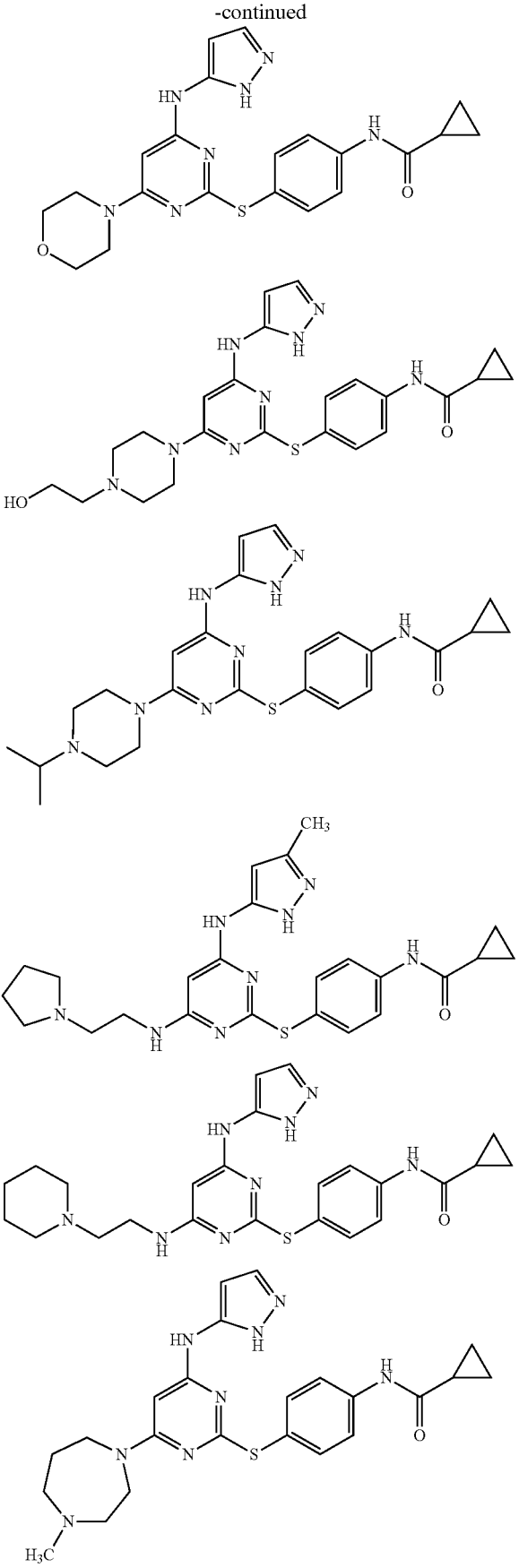
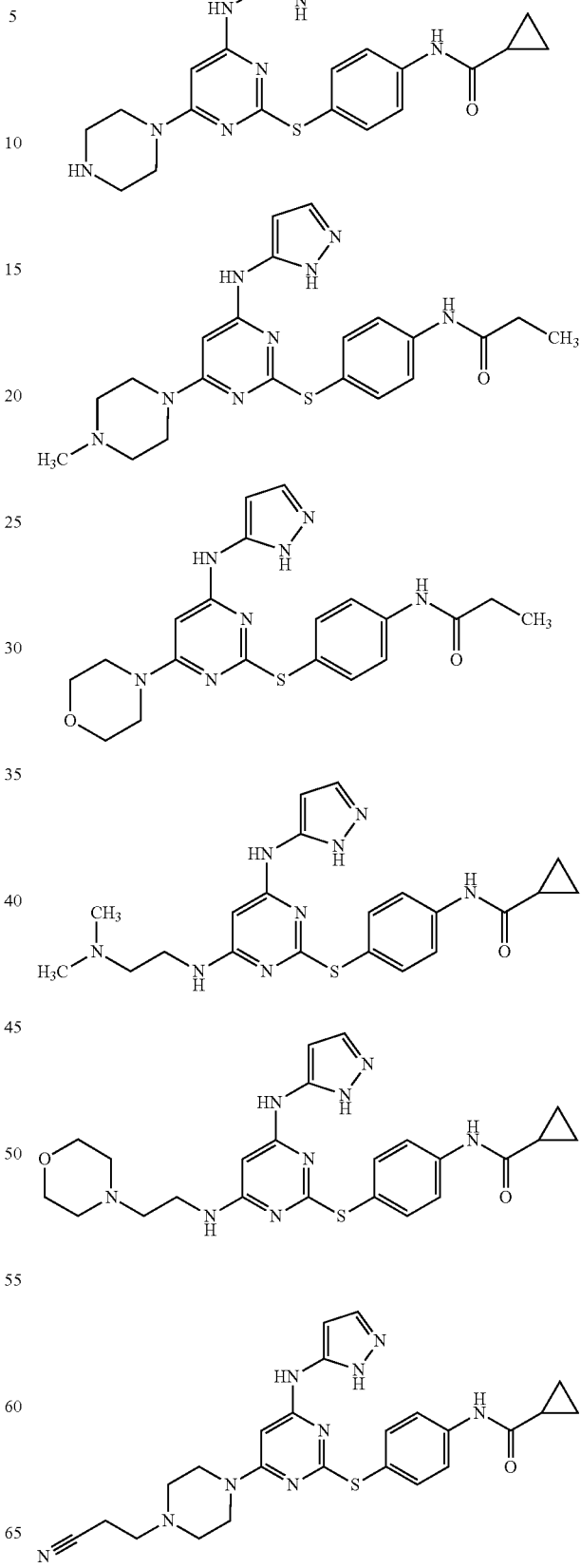

-continued
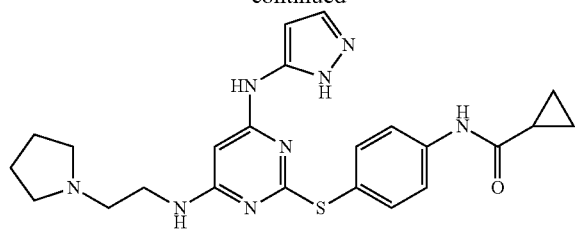
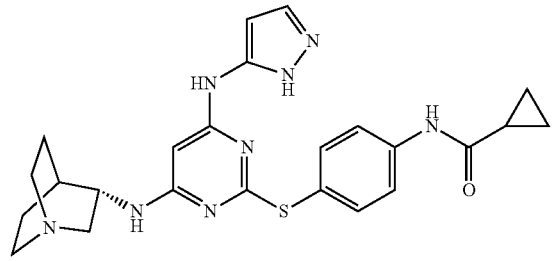
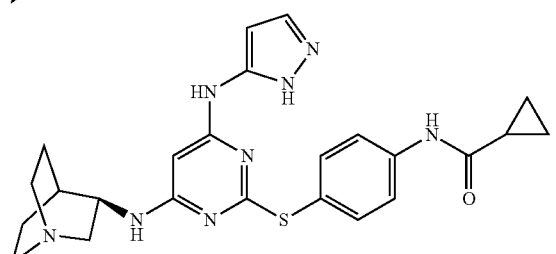
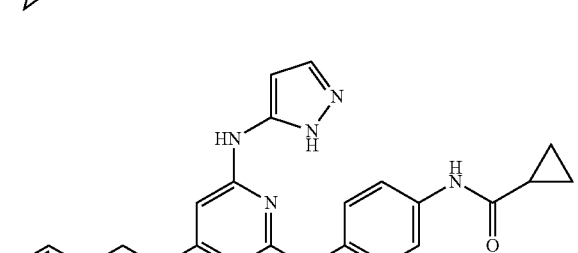
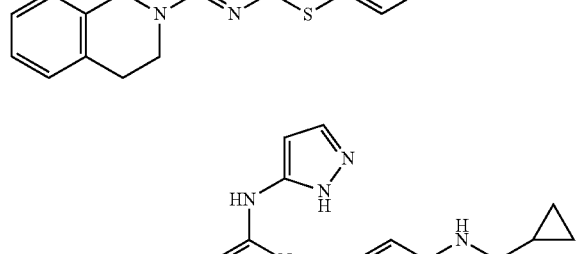
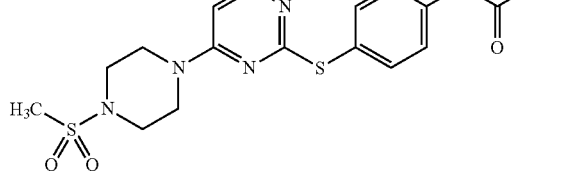
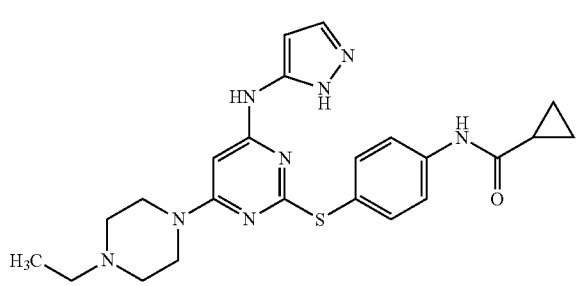
-continued
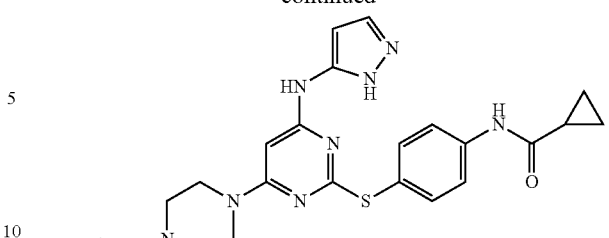
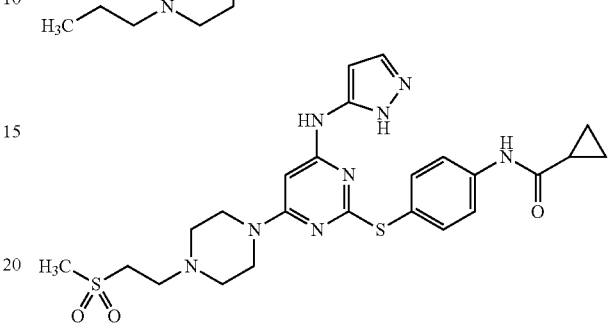
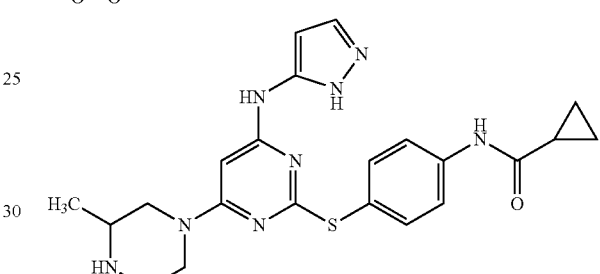
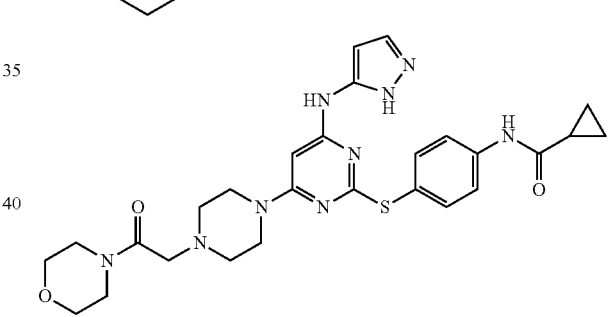
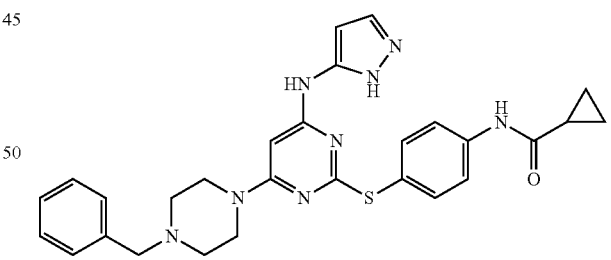
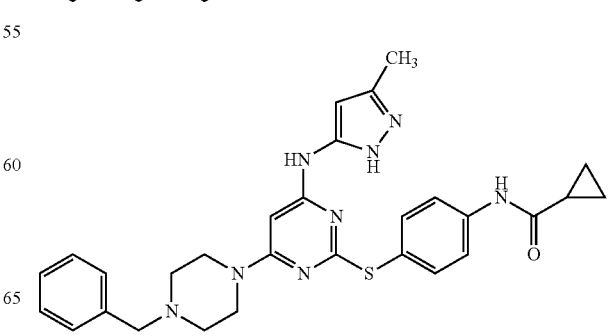

-continued
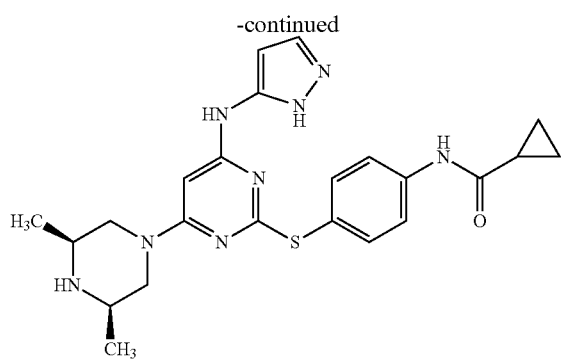
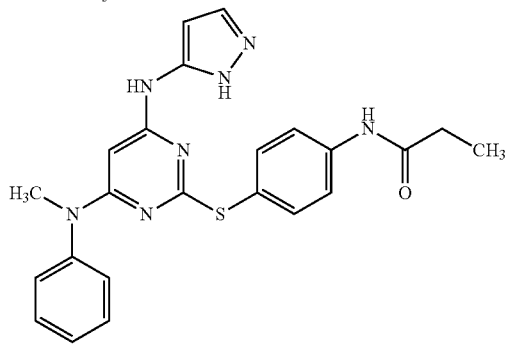
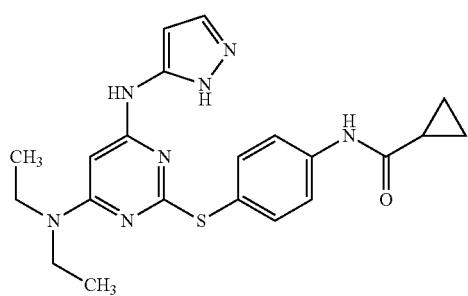
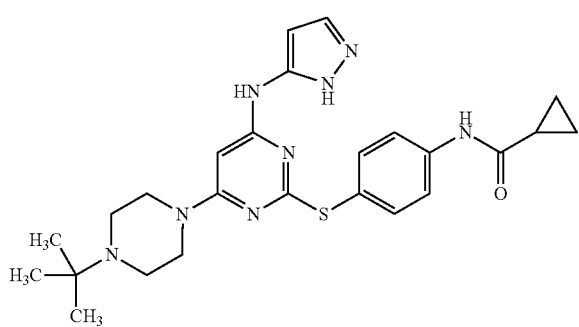
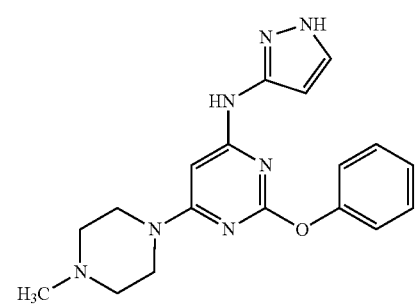
-continued
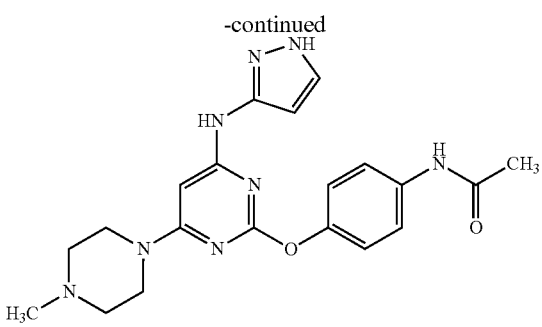
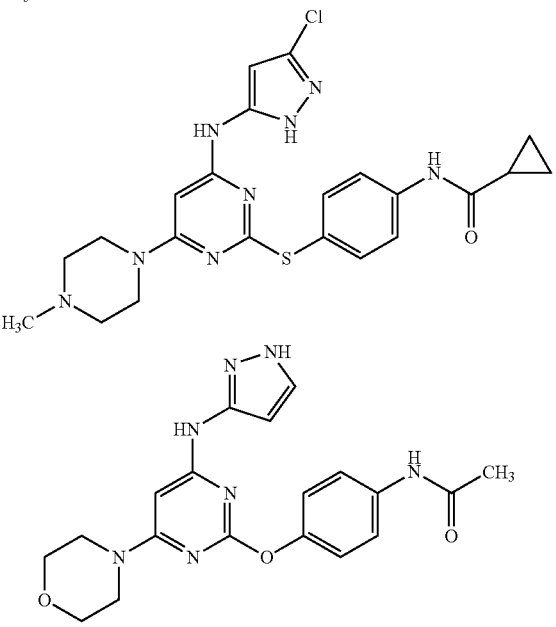
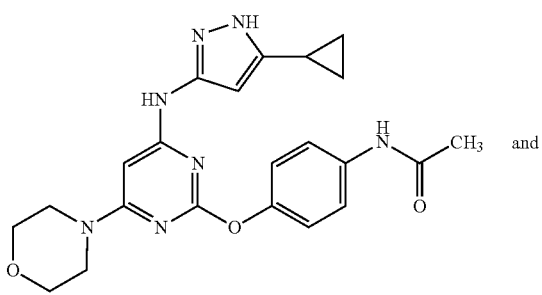
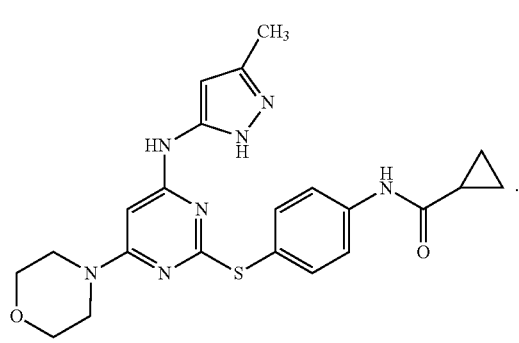
In particular embodiments of the presently disclosed methods, the compound of Formula (I) is:

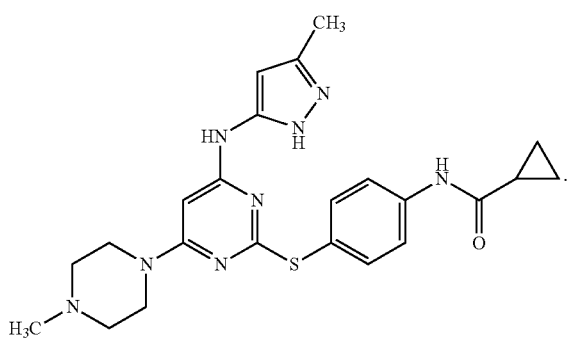

Additional aminopyrimidines useful as inhibitors of protein kinases are disclosed in International PCT Patent Application Publication Nos. WO2007/056221 and WO2007/056164, each of which is incorporated herein by reference in their entirety.

Accordingly, in some embodiments, the presently disclosed subject matter relates to compounds, and methods of use thereof, which can promote the survival and/or neurite outgrowth of retinal ganglion cells (RGCs). In some embodiments, a compound of Formula (I), or a pharmaceutically acceptable salt thereof, can prevent the death of one or more damaged neuronal cells. In other embodiments, a compound of Formula (I) can be used to promote the growth or regeneration of all or part of a neuronal cell, including, but not limited to, the growth of a neurite, such as an axon, a dendrite, and the like.

As used herein, a "neuron or portion thereof" can consist of or be a portion of a neuron selected from the group consisting of a cerebellar granule neuron, a dorsal root ganglion neuron, a cortical neuron, a sympathetic neuron, and a hippocampal neuron. More particularly, the term "neuron" as used herein denotes nervous system cells that include a central cell body or soma, and two types of extensions or projections: dendrites, by which, in general, the majority of neuronal signals are conveyed to the cell body; and axons, by which, in general, the majority of neuronal signals are conveyed from the cell body to effector cells, such as target neurons or muscle. Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column). Certain specific examples of neuron types that may be subject to treatment according to the presently disclosed subject matter include cerebellar granule neurons, dorsal root ganglion neurons, and cortical neurons. Further, as used herein, the term "neurite" means a projection from the cell body of a neuron including, e.g., an axon or a dendrite.

Without wishing to be bound to any one particular theory, it is believed that the presently disclosed compounds can modulate: (i) the activity or expression of a target protein in the neuron or portion thereof; (ii) a process in the neuron or portion thereof; or (iii) a biological pathway associated with a neurodegenerative disease, disorder, or condition. In particular embodiments, the presently disclosed compounds inhibit one or more protein kinases involved in a biological pathway associated with a neurodegenerative disease, disorder, or condition. As used herein, the term "inhibit" or "inhibits" means to decrease, suppress, attenuate, diminish, arrest, or stabilize the development or progression of a disease, disorder, or condition, or the activity of a biological pathway, e.g., by at least 10%, 20%, 30%, 40%, 50%, 60%, 70%, 80%, 90%, 95%, 98%, 99%, or even 100% compared to an untreated control subject, cell, or biological pathway. By the term "decrease" is meant to inhibit, suppress, attenuate, diminish, arrest, or stabilize a symptom of a neurodegenerative disease, disorder, or condition. It will be appreciated that, although not precluded, treating a disease, disorder or condition does not require that the disease, disorder, condition or symptoms associated therewith be completely eliminated.

In some embodiments, the neuron or portion thereof can be present in a subject, such as a human subject. The subject can, for example, have or be at risk of developing a disease, disorder, or condition selected from the group consisting of (i) a disease, disorder, or condition of the nervous system; (ii) a condition of the nervous system that is secondary to a disease, disorder, or condition, or a therapy having a primary effect outside of the nervous system; (iii) an injury to the nervous system, such as, for example, an injury caused by physical, mechanical, or chemical trauma; (iv) pain; (v) ocular-related neurodegeneration; (vi) memory loss; and (vii) a psychiatric disorder.

Accordingly, in some embodiments, a compound of Formula (I) can be used to treat or prevent a neurodegenerative disease, disorder, or condition. As used herein, the terms "treat," "treating," "treatment," and the like, are meant to decrease, suppress, attenuate, diminish, arrest, the underlying cause of a disease, disorder, or condition, or to stabilize the development or progression of a disease, disorder, condition, and/or symptoms associated therewith. The terms "treat," "treating," "treatment," and the like, as used herein can refer to curative therapy, prophylactic therapy, and preventative therapy. The treatment, administration, or therapy can be consecutive or intermittent. Consecutive treatment, administration, or therapy refers to treatment on at least a daily basis without interruption in treatment by one or more days. Intermittent treatment or administration, or treatment or administration in an intermittent fashion, refers to treatment that is not consecutive, but rather cyclic in nature. Treatment according to the presently disclosed methods can result in complete relief or cure from a disease, disorder, or condition, or partial amelioration of one or more symptoms of the disease, disease, or condition, and can be temporary or permanent. The term "treatment" also is intended to encompass prophylaxis, therapy and cure.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

By "agent" is meant a compound of Formula (I) or another agent, e.g., a peptide, nucleic acid molecule, or other small molecule compound administered in combination with a compound of Formula (I). More generally, the term "therapeutic agent" means a substance that has the potential of affecting the function of an organism. Such an agent may be, for example, a naturally occurring, semi-synthetic, or synthetic agent. For example, the therapeutic agent may be a drug that targets a specific function of an organism. A therapeutic agent also may be a nutrient. A therapeutic agent may decrease, suppress, attenuate, diminish, arrest, or stabilize the development or progression of disease, disorder, or condition in a host organism.

The term "administering" as used herein refers to contacting a neuron or portion thereof with a compound of Formula (I). This term includes administration of the presently disclosed compounds to a subject in which the neuron or portion thereof is present, as well as introducing the presently disclosed compounds into a medium in which a neuron or portion thereof is cultured.

By "neurodegenerative disease, disorder, or condition" is meant a disease, disorder, or condition (including a neuropathy) associated with degeneration or dysfunction of neurons or other neural cells, such as retinal ganglion cells. A neurodegenerative disease, disorder, or condition can be any disease, disorder, or condition in which decreased function or dysfunction of neurons, or loss or neurons or other neural cells, can occur. Particular targets associated with neurodegenerative diseases, disorders, or conditions are disclosed in International PCT Patent Application Publication No. WO2011/050192 to Lewcock et al., published Apr. 28, 2011, which is incorporated herein by reference in its entirety. As used herein, the term "disorder" in general refers to any condition that would benefit from treatment with a compound of Formula (I), including any disease, disorder, or condition that can be treated by an effective amount of a compound of Formula (I), or a pharmaceutically acceptable salt thereof.

Such diseases, disorders, or conditions include, but are not limited to, glaucoma, and neurodegenerative diseases, disorders, or conditions of the nervous systems, such as or associated with amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, Alzheimer's disease, Huntington's disease, Parkinson's disease, Parkinson's-plus diseases, multiple system atrophy, progressive supranuclear palsy, corticobasal degeneration, dementia with Lewy bodies, frontotemporal dementia, demyelinating diseases, Guillain-Barre syndrome, multiple sclerosis, Charcot-Marie-Tooth disease, prion diseases, Creutzfeldt-Jakob disease, Gerstmann-Straussler-Scheinker syndrome (GSS), fatal familial insomnia (FFI), bovine spongiform encephalopathy (BSE), Pick's disease, epilepsy, and AIDS demential complex.

Other neurodegenerative diseases, disorders, or conditions of the nervous systems, such as or associated with alcoholism, Alexander's disease, Alper's disease, ataxia telangiectasia, Batten disease (also known as Spielmeyer-Vogt-Sjogren-Batten disease), Canavan disease, Cockayne syndrome, diabetic neuropathy, frontotemporal lobar degeneration, HIV-associated dementia, Kennedy's disease, Krabbe's disease, neuroborreliosis, Machado-Joseph disease (Spinocerebellar ataxia type 3), wet or dry macular degeneration, Niemann Pick disease, Pelizaeus-Merzbacher Disease, photoreceptor degenerative diseases, such as retinitis pigmentosa and associated diseases, Refsum's disease, Sandhoffs disease, Schilder's disease, subacute combined degeneration of spinal cord secondary to pernicious anemia, Spielmeyer-Vogt-Sjogren-Batten disease (also known as Batten disease), spinocerebellar ataxia (multiple types with varying characteristics), Steele-Richardson-Olszewski disease, and tabes dorsalis.

Examples of ocular-related neurodegeneration include, but are not limited to, glaucoma, lattice dystrophy, retinitis pigmentosa, age-related macular degeneration (AMD), photoreceptor degeneration associated with wet or dry AMD, other retinal degeneration, optic nerve drusen, optic neuropathy, and optic neuritis.

Non-limiting examples of different types of glaucoma that can be prevented or treated according to the presently disclosed subject matter include primary glaucoma (also known as primary open-angle glaucoma, chronic open-angle glaucoma, chronic simple glaucoma, and glaucoma simplex), low-tension glaucoma, primary angle-closure glaucoma (also known as primary closed-angle glaucoma, narrow-angle glaucoma, pupil-block glaucoma, and acute congestive glaucoma), acute angle-closure glaucoma, chronic angle-closure glaucoma, intermittent angle-closure glaucoma, chronic open-angle closure glaucoma, pigmentary glaucoma, exfoliation glaucoma (also known as pseudoexfoliative glaucoma or glaucoma capsulare), developmental glaucoma (e.g., primary congenital glaucoma and infantile glaucoma), secondary glaucoma (e.g., inflammatory glaucoma (e.g., uveitis and Fuchs heterochronic iridocyclitis)), phacogenic glaucoma (e.g., angle-closure glaucoma with mature cataract, phacoanaphylactic glaucoma secondary to rupture of lens capsule, phacolytic glaucoma due to phacotoxic meshwork blockage, and subluxation of lens), glaucoma secondary to intraocular hemorrhage (e.g., hyphema and hemolytic glaucoma, also known as erythroclastic glaucoma), traumatic glaucoma (e.g., angle recession glaucoma, traumatic recession on anterior chamber angle, postsurgical glaucoma, aphakic pupillary block, and ciliary block glaucoma), neovascular glaucoma, drug-induced glaucoma (e.g., corticosteroid induced glaucoma and alpha-chymotrypsin glaucoma), toxic glaucoma, and glaucoma associated with intraocular tumors, retinal detachments, severe chemical burns of the eye, and iris atrophy. In certain embodiments, the neurodegenerative disease, disorder, or condition is a disease, disorder, or condition that is not associated with excessive angiogenesis, for example, a glaucoma that is not neovascular glaucoma.

Examples of conditions of the nervous system that are secondary to a disease, disorder, condition, or therapy having a primary effect outside of the nervous system include, but are not limited to, peripheral neuropathy or neuralgia caused by diabetes, cancer, AIDS, hepatitis, kidney dysfunction, Colorado tick fever, diphtheria, HIV infection, leprosy, Lyme disease, polyarteritis nodosa, rheumatoid arthritis, sarcoidosis, Sjogren syndrome, syphilis, systemic lupus erythematosus, and amyloidosis.

Examples of pain include, but are not limited to, chronic pain, fibromyalgia, spinal pain, carpel tunnel syndrome, pain from cancer, arthritis, sciatica, headaches, pain from surgery, muscle spasms, back pain, visceral pain, pain from injury, dental pain, neuralgia, such as neuogenic or neuropathic pain, nerve inflammation or damage, shingles, herniated disc, a torn ligament, and diabetes.

Examples of injuries to the nervous system caused by physical, mechanical, or chemical trauma include, but are not limited to, nerve damage caused by exposure to toxic compounds, heavy metals (e.g., lead, arsenic, and mercury), industrial solvents, drugs, chemotherapeutic agents, dapsone, HIV medications (e.g., zidovudine, didanosine, stavudine, zalcitabine, ritonavir, and amprenavir), cholesterol lowering drugs (e.g., lovastatin, indapamide, and gemfibrozil), heart or blood pressure medications (e.g., amiodarone, hydralazine, perhexyline), and metronidazole.

Further examples also include burn, wound, surgery, accidents, ischemia, prolonged exposure to cold temperature (e.g., frost bite), stroke, intracranial hemorrhage, and cerebral hemorrhage. More particularly, traumatic injury or other damage to neuronal cells (e.g., trauma due to accident, bluntforce injury, gunshot injury, spinal cord injury, ischemic conditions of the nervous system such as stroke, cell damage due to aging or oxidative stress, and the like) also is intended to be included within the language "neurodegenerative disease, disorder, or condition." In such embodiments, the presently disclosed methods can be used to treat neuronal damage due to traumatic injury or stroke by preventing death of damaged neuronal cells and/or by promoting or stimulating neurite growth from damaged neuronal cells.

Examples of psychiatric disorders include, but are not limited to, schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, e.g., optic crush experiments, and the like).

In particular embodiments, the subject is suffering from or susceptible to a neurodegenerative disease, disorder, or condition, such as glaucoma, e.g., a subject diagnosed as suffering from or susceptible to a neurodegenerative disease, disorder, or condition. In other embodiments, the subject has been identified (e.g., diagnosed) as suffering from or susceptible to a neurodegenerative disease, disorder, or condition (including traumatic injury) in which neuronal cell loss is implicated, or in which damage to neurites is involved, and for which treatment or prophylaxis is desired.

In certain embodiments, the subject is not suffering, or has not been diagnosed as suffering, from cancer. In certain embodiments, the subject is not suffering, or has not been diagnosed as suffering, from a disorder related to excess angiogenesis. In certain embodiments in which a cell is contacted with a compound of Formula (I), or a pharmaceutically acceptable salt thereof, the cell is not a neoplastic cell. In certain embodiments of the above aspects, the cell is a mammalian cell, more preferably a human cell.

In some embodiments, the presently disclosed methods produce at least about a 10%, 15%, 20%, 25%, 30%, 35%, 40%, 45%, 50%, 55%, 60%, 65%, 70%, 75%, 80%, 85%, 90%, 95%, or even 100% decrease in cell loss or loss of function relative to cell survival or cell function measured in absence of the tested compound, i.e., a control sample, in an assay. In other embodiments, the compounds and amounts for use in the presently disclosed therapeutic methods produce at least about 10% to 15% increase in neuron count, neuron function, neurite count, neurite total length, or neurite average length relative to absence of the tested compound in an assay.

In any of the above-described methods, the administering of a compound of Formula (I) can result in at least about a 10%, 15%, 20%, 25%, 30%, 35%, 40%, 45%, 50%, 55%, 60%, 65%, 70%, 75%, 80%, 85%, 90%, 95%, or even 100% decrease in one or more (e.g., 1, 2, 3, 4, 5, 6, 7, 8. 9, or 10) symptoms of a disease, disorder, or condition of the nervous system; a condition of the nervous system that is secondary to a disease, disorder, condition, or therapy having a primary effect outside of the nervous system; injury to the nervous system caused by physical, mechanical, or chemical trauma; pain; ocular-related neurodegeneration; memory loss; or psychiatric disorder, compared to a subject that is not administered the one or more of the agents described herein.

Non-limiting examples of such symptoms include, but are not limited to, tremors, slowness of movement, ataxia, loss of balance, depression, decreased cognitive function, short-term memory loss, long-term memory loss, confusion, changes in personality, language difficulties, loss of sensory perception, sensitivity to touch, numbness in extremities, muscle weakness, muscle paralysis, muscle cramps, muscle spasms, significant changes in eating habits, excessive fear or worry, insomnia, delusions, hallucinations, fatigue, back pain, chest pain, digestive problems, headache, rapid heart rate, dizziness, blurred vision, shadows or missing areas of vision, metamorphopsia, impairment in color vision, decreased recovery of visual function after exposure to bright light, and loss in visual contrast sensitivity.

In any of the above-described methods, the administering of a compound of Formula (I) results in at least about a 10%, 15%, 20%, 25%, 30%, 35%, 40%, 45%, 50%, 55%, 60%, 65%, 70%, 75%, 80%, 85%, 90%, 95%, or even 100% decrease in the likelihood of developing a disease, disorder, or condition of the nervous system; condition of the nervous system that is secondary to a disease, disorder, condition, or therapy having a primary effect outside of the nervous system; injury to the nervous system caused by physical, mechanical, or chemical trauma; pain; ocular-related neurodegeneration; memory loss; or psychiatric disorder, compared to a control population of subjects that are not administered a compound of Formula (I).

The administration of one or more agent as described herein may result in at least about a 10%, 15%, 20%, 25%, 30%, 35%, 40%, 45%, 50%, 55%, 60%, 65%, 70%, 75%, 80%, 85%, 90%, 95%, or even 100% decrease in the number of neurons (or neuron bodies, axons, or dendrites thereof) that degenerate in a neuron population or in a subject compared to the number of neurons (or neuron bodies, axons, or dendrites thereof) that degenerate in neuron population or in a subject that is not administered the one or more of the agents described herein.

In some embodiments, the presently disclosed methods include preventing or inhibiting neuron or axon degeneration. The phrases "preventing axon degeneration," "preventing neuron degeneration," "inhibiting axon degeneration," or "inhibiting neuron degeneration" as used herein include: (i)

the ability to inhibit or prevent axon or neuron degeneration in patients newly diagnosed as having a neurodegenerative disease or at risk of developing a new neurodegenerative disease; and (ii) the ability to inhibit or prevent further axon or neuron degeneration in patients who are already suffering from, or have symptoms of, a neurodegenerative disease. Preventing axon or neuron degeneration includes decreasing or inhibiting axon or neuron degeneration, which may be characterized by complete or partial inhibition of neuron or axon degeneration. Such prevention or inhibition can be assessed, for example, by analysis of neurological function. Further, the phrases "preventing neuron degeneration" and "inhibiting neuron degeneration" include such inhibition with respect to the entire neuron or a portion thereof, such as the neuron cell body, axons, and dendrites.

The above-listed terms also include in vitro and ex vivo methods. For example, in certain embodiments, the presently disclosed methods are applicable to cell culture techniques wherein it is desirable to prevent neuronal cell death or loss of neuronal function. In vitro neuronal culture systems have proved to be fundamental and indispensable tools for the study of neural development, as well as the identification of neurotrophic factors, such as nerve growth factor (NGF), ciliary trophic factors (CNTF), and brain derived neurotrophic factor (BDNF). One use of certain embodiments of the presently disclosed methods is in cultures of neuronal cells, such as in the use of such cultures for the generation of new neurons and glia. In such embodiments, the cultured cells can be contacted with a compound of Formula (I) to prevent neuronal cell death or loss of neuronal function. In an exemplary embodiment, the subject method can be used to culture, for example, sensory neurons or, alternatively, motoneurons. Such neuronal cultures can be used as convenient assay systems, as well as sources of implantable cells for therapeutic treatments.

In other examples, the neuron or portion thereof treated according to the presently disclosed methods is ex vivo or in vitro. Accordingly, the presently disclosed compounds can be useful as components of culture media for use in culturing nerve cells in vitro. More particularly, in certain embodiments, the presently disclosed methods can be used to improve the survival or integration of transplanted neuronal cells into a host subject (e.g., through a nerve graft or nerve transplant). Thus, for example, a subject receiving a transplant of neuronal cells can be treated (before, during, or after the transplantation procedure) with compounds according to the presently disclosed methods, to prevent cell death of the transplanted cells (or host cells that may be perturbed during the transplantation procedure), and/or to promote the growth of neurites in the transplanted cells or the host neuronal cells, and thereby promote integration of the transplanted cells into the host nervous system.

The presently disclosed subject matter further provides methods of modulating the growth, cell size, and/or proliferation of a neuron (e.g., cerebellar granule neuron, a dorsal root ganglion neuron, a cortical neuron, or a sympathetic neuron) by contacting a neuron with a compound of Formula (I).

C. Pharmaceutical Compositions

The presently disclosed pharmaceutical compositions and formulations include pharmaceutical compositions of compounds of Formula (I), alone or in combination with one or more additional therapeutic agents, in admixture with a physiologically compatible carrier, which can be administered to a subject, for example, a human subject, for therapeutic or prophylactic treatment. As used herein, "physiologically compatible carrier" refers to a physiologically acceptable diluent including, but not limited to water, phosphate buffered saline, or saline, and, in some embodiments, can include an adjuvant. Acceptable carriers, excipients, or stabilizers are nontoxic to recipients at the dosages and concentrations employed, and can include buffers such as phosphate, citrate, and other organic acids; antioxidants including ascorbic acid, BHA, and BHT; low molecular weight (less than about 10 residues) polypeptides; proteins, such as serum albumin, gelatin or immunoglobulins; hydrophilic polymers, such as polyvinylpyrrolidone, amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or nonionic surfactants such as Tween, Pluronics, or PEG. Adjuvants suitable for use with the presently disclosed compositions include adjuvants known in the art including, but not limited to, incomplete Freund's adjuvant, aluminum phosphate, aluminum hydroxide, and alum.

Compositions to be used for in vivo administration must be sterile, which can be achieved by filtration through sterile filtration membranes, prior to or following lyophilization and reconstitution. Therapeutic compositions may be placed into a container having a sterile access port, for example, an intravenous solution bag or vial having a stopper pierceable by a hypodermic injection needle.

One of skill in the art will recognize that the pharmaceutical compositions include the pharmaceutically acceptable salts of the compounds described above. The term "pharmaceutically acceptable salts" is meant to include salts of active compounds, which are prepared with relatively nontoxic acids or bases, depending on the particular substituent moieties found on the compounds described herein.

When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include alkali or alkaline earth metal salts including, but not limited to, sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids including, but not limited to, hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids, such as acetic (acetates), propionic (propionates), isobutyric (isobutyrates), maleic (maleates), malonic, benzoic (benzoates), succinic (succinates), suberic, fumaric (fumarates), lactic (lactates), mandelic (mandelates), phthalic (phthalates), benzenesulfonic (benzosulfonates), p-tolylsulfonic, citric (citrates), tartaric (tartrates, e.g., (+)-tartrates, (−)-tartrates or mixtures thereof including racemic mixtures), methanesulfonic, and the like. Other pharmaceutically acceptable salts, include, but are not limited to, besylate, bicarbonate, bitartrate, bromide, calcium edetate, carnsylate, carbonate, edetate, edisylate, estolate, esylate, gluceptate, gluconate, glutamate, glycollylarsanilate, hexylresorcinate, hydrabamine, hydroxynaphthoate, iodide, isethionate, lactobionate, malate, mesylate, mucate, napsylate, nitrate, pamoate (embonate), pantothenate, phosphate/diphosphate, polygalacturonate, salicylate, stearate, subacetate, sulfate, tannate, and teoclate, also are included.

Also included are salts of amino acids, such as arginate and the like, and salts of organic acids, such as, glucuronic or galactunoric acids, and the like. See, for example, Berge et al, "Pharmaceutical Salts", Journal of Pharmaceutical Science, 1977, 66, 1-19. Some compounds of the present disclosure can contain both basic and acidic functionalities, which allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties. For example, salts tend to be more soluble in aqueous or other protonic solvents than are the corresponding free base forms.

In particular embodiments, the pharmaceutically acceptable salt of a compound of Formula (I) is selected from the group consisting of HCl, a sulfonate, a sulfate, phosphate, a malonate, a succinate, a fumarate, a maleate, a tartrate, a 3-sulfopropanoic acid salt, and a citrate. Suitable salts of the presently disclosed compounds are disclosed in International PCT Patent Application Publication No. WO2004/000833 to Charrier et al., published Dec. 31, 2003, which is incorporated herein by reference in its entirety.

Certain compounds of the present disclosure can exist in unsolvated forms, as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds that can be in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

D. Combination Therapies

In certain embodiments, presently disclosed subject matter also includes combination therapies. Depending on the particular disease, disorder, or condition to be treated or prevented, additional therapeutic agents, which are normally administered to treat or prevent that condition, may be administered in combination with the compounds of this disclosure. These additional agents may be administered separately, as part of a multiple dosage regimen, from the composition comprising a compound of Formula (I). Alternatively, these agents may be part of a single dosage form, mixed together with the compound of Formula (I) in a single composition.

By "in combination with" is meant the administration of a compound of Formula (I) with one or more therapeutic agents either simultaneously, sequentially, or a combination thereof. Therefore, a cell or a subject administered a combination of a compound of Formula (I) can receive a compound of Formula (I) and one or more therapeutic agents at the same time (i.e., simultaneously) or at different times (i.e., sequentially, in either order, on the same day or on different days), so long as the effect of the combination of both agents is achieved in the cell or the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of Formula (I) and one or more therapeutic agents are administered simultaneously, they can be administered to the cell or administered to the subject as separate pharmaceutical compositions, each comprising either a compound of Formula (I) or one or more therapeutic agents, or they can contact the cell as a single composition or be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered compound is not diminished by the sequential, simultaneous or separate administration of the subsequent compound(s).

A compound of Formula (I) can be used in therapy in combination with one or more other compounds used to treat a neurodegenerative disease, disorder, or condition. For example, a compound of Formula (I) can be co-administered in combination with one or more other compounds, for example, at a ratio in the range of 1:1-1:5-5:1, 1:1-1:10-10:1, 1:1-1:25-25:1, 1:1-1:100-100:1, 1:1-1:1000-1000:1 or 1:1-1:10,000-10,000:1, and the like. For example, in the treatment of glaucoma, other anti-glaucoma medicaments can be used in combination with compounds of Formula (I), including, but not limited to, beta-blockers, including levobunolol (BETAGAN), timolol (BETIMOL, TIMOPTIC), betaxolol (BETOPTIC) and metipranolol (OPTIPRANOLOL); alpha-agonists, such as apraclonidine (IOPIDINE) and brimonidine (ALPHAGAN); carbonic anhydrase inhibitors, such as acetazolamide, methazolamide, dorzolamide (TRUSOPT) and brinzolamide (AZOPT); prostaglandins or prostaglandin analogs such as latanoprost (XALATAN), bimatoprost (LUMIGAN) and travoprost (TRAVATAN); miotic or cholinergic agents, such as pilocarpine (ISOPTO CARPINE, PILOPINE) and carbachol (ISOPTO CARBACHOL); epinephrine compounds, such as dipivefrin (PROPINE); forskolin; or neuroprotective compounds, such as brimonidine and memantine. In certain embodiments, the compound used in combination with a compound of Formula (I) is not an anti-angiogenic agent, such as a steroid derivative, such as 2-methoxyestradiol or analogs or derivatives thereof. In other embodiments, the additional therapeutic agent can be an antibiotic.

The presently disclosed compounds of Formula (I) can be optionally combined with or administered in concert with each other or other agents known to be useful in the treatment of the relevant disease, disorder, or condition. Thus, in the treatment of ALS, for example, the presently disclosed compounds can be administered in combination with Riluzole (RILUTEK), minocycline, insulin-like growth factor 1 (IGF-1), and/or methylcobalamin. In another example, in the treatment of Parkinson's disease, the presently disclosed compounds can be administered with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In a further example, in the treatment of Alzheimer's disease, the presently disclosed compounds can be administered with acetylcholinesterase inhibitors (e.g., donepezil, galantamine, and rivastigmine) and/or NMDA receptor antagonists (e.g., memantine). The combination therapies can involve concurrent or sequential administration, by the same or different routes, as determined to be appropriate by those of skill in the art. The presently disclosed subject matter also includes pharmaceutical compositions and kits including combinations as described herein.

In other embodiments, the presently disclosed subject matter includes a combination therapy of administering a compound of Formula (I) in combination with surgery, e.g., surgical relief of intraocular pressure, e.g., via trabeculectomy, laser trabeculoplasty, or drainage implants, and the like.

E. Dosage and Mode of Administration

The presently disclosed pharmaceutical compositions can be administered using a variety of methods known in the art depending on the subject and the particular disease, disorder, or condition being treated. The administering can be carried out by, for example, intravenous infusion; injection by intravenous, intraperitoneal, intracerebral, intramuscular, intraocular, intraarterial or intralesional routes; or topical or ocular application.

More particularly, as described herein, the presently disclosed compounds can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articullar, intra-sternal, intrasynovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art. For example, for ocular administration, an eyedrop formulation can include an effective concentration of a compound of Formula (I) together with other components, such as buffers, wetting agents and the like. Intravitreal injection also may be employed to administer a presently disclosed compound to the eye.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

For intracerebral use, the compounds can be administered continuously by infusion into the fluid reservoirs of the CNS, although bolus injection may be acceptable. The presently disclosed compounds can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the presently disclosed compounds can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

The presently disclosed pharmaceutical compositions can be manufactured in a manner known in the art, e.g. by means of conventional mixing, dissolving, granulating, dragee-making, levitating, emulsifying, encapsulating, entrapping or lyophilizing processes.

More particularly, pharmaceutical compositions for oral use can be obtained through combination of active compounds with a solid excipient, optionally grinding a resulting mixture, and processing the mixture of granules, after adding suitable auxiliaries, if desired, to obtain tablets or dragee cores. Suitable excipients include, but are not limited to, carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl cellulose; and gums including arabic and tragacanth; and proteins, such as gelatin and collagen; and polyvinylpyrrolidone (PVP:povidone). If desired, disintegrating or solubilizing agents, such as cross-linked polyvinyl pyrrolidone, agar, alginic acid, or a salt thereof, such as sodium alginate, also can be added to the compositions.

Dragee cores are provided with suitable coatings, such as concentrated sugar solutions, which also can contain gum arabic, talc, polyvinylpyrrolidone, carbopol gel, polyethylene glycol (PEG), and/or titanium dioxide, lacquer solutions, and suitable organic solvents or solvent mixtures. Dyestuffs or pigments can be added to the tablets or dragee coatings for product identification or to characterize the quantity of active compound, e.g., dosage, or different combinations of active compound doses.

Pharmaceutical compositions suitable for oral administration include push-fit capsules made of gelatin, as well as soft, sealed capsules made of gelatin and a coating, e.g., a plasticizer, such as glycerol or sorbitol. The push-fit capsules can contain active ingredients admixed with a filler or binder, such as lactose or starches, lubricants, such as talc or magnesium stearate, and, optionally, stabilizers. In soft capsules, the active compounds can be dissolved or suspended in suitable liquids, such as fatty oils, liquid paraffin, or liquid polyethylene glycols (PEGs), with or without stabilizers. Stabilizers can be added as warranted.

In some embodiments, the presently disclosed pharmaceutical compositions can be administered by rechargeable or biodegradable devices. For example, a variety of slow-release polymeric devices have been developed and tested in vivo for the controlled delivery of drugs, including proteinaceous biopharmaceuticals. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly (2-hydroxyethyl-methacrylate) (Langer et al., J. Biomed. Mater. Res. 15:167, 1981; Langer, Chem. Tech. 12:98, 1982), ethylene vinyl acetate (Langer et al., Id), or poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et at, Proc. Natl. Acad. Sci. U.S.A. 77:4030, 1980; U.S. Pat. Nos. 4,485,045 and 4,544, 545; and EP 102,324A). Ordinarily, the liposomes are of the small (about 200-800 Angstroms) unilamelar type in which the lipid content is greater than about 30 mol % cholesterol, the selected proportion being adjusted for the optimal therapy. Such materials can comprise an implant, for example, for sustained release of the presently disclosed compounds, which, in some embodiments, can be implanted at a particular, pre-determined target site.

Pharmaceutical compositions for parenteral administration include aqueous solutions of active compounds. For injection, the presently disclosed pharmaceutical compositions can be formulated in aqueous solutions, for example, in some embodiments, in physiologically compatible buffers, such as Hank's solution, Ringer' solution, or physiologically buffered saline. Aqueous injection suspensions can contain substances that increase the viscosity of the suspension, such as sodium carboxymethyl cellulose, sorbitol, or dextran. Additionally, suspensions of the active compounds or vehicles include fatty oils, such as sesame oil, or synthetic fatty acid esters, such as ethyl oleate or triglycerides, or liposomes. Optionally, the suspension also can contain suitable stabilizers or agents that increase the solubility of the compounds to allow for the preparation of highly concentrated solutions.

For nasal or transmucosal administration generally, penetrants appropriate to the particular barrier to be permeated are used in the formulation. Such penetrants are generally known in the art.

For inhalation delivery, the agents of the disclosure also can be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

In other embodiments, the pharmaceutical composition can be a lyophilized powder, optionally including additives, such as 1 mM-50 mM histidine, 0.1%-2% sucrose, 2%-7% mannitol at a pH range of 4.5 to 5.5 that is combined with buffer prior to use.

The presently disclosed subject matter also includes the use of a compound of Formula (I) in the manufacture of a medicament for neuroprotection.

Regardless of the route of administration selected, the presently disclosed compounds, which may be used in a suitable hydrated form, and/or the pharmaceutical compositions are formulated into pharmaceutically acceptable dosage forms such as described below or by other conventional methods known to those of skill in the art.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition (e.g., a disease, condition, or disorder related to loss of neuronal cells or cell function), or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

Actual dosage levels of the active ingredients in the presently disclosed pharmaceutical compositions can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular compound employed, or salt thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of Formula (I) employed in the pharmaceutical composition at levels lower than that required to achieve the desired therapeutic effect and gradually increase the dosage until the desired effect is achieved. Accordingly, the dosage range for administration will be adjusted by the physician as necessary. It will be appreciated that an amount of a compound required for achieving the desired biological response, e.g., neuroprotective activity, may be different from the amount of compound effective for another purpose.

In general, a suitable daily dose of a compound of Formula (I) will be that amount of the compound that is the lowest dose effective to produce a therapeutic effect. Such an effective dose will generally depend upon the factors described above. Generally, doses of the compounds of Formula (I) will range from about 0.0001 to about 1000 mg per kilogram of body weight of the subject per day. In certain embodiments, the dosage is between about 1 µg/kg and about 500 mg/kg, more preferably between about 0.01 mg/kg and about 50 mg/kg. For example, in certain embodiments, a dose can be about 1, 5, 10, 15, 20, or 40 mg/kg/day.

If desired, the effective daily dose of the active compound can be administered as two, three, four, five, six or more sub-doses administered separately at appropriate intervals throughout the day, optionally, in unit dosage forms.

F. Kits or Pharmaceutical Systems

The presently disclosed compounds and compositions can be assembled into kits or pharmaceutical systems for use in treating or preventing neurodegenerative diseases, disorders, or conditions. In some embodiments, the presently disclosed kits or pharmaceutical systems include a compound of Formula (I) or (Ia), or pharmaceutically acceptable salts thereof. In particular embodiments, the compounds of Formula (I) or (Ia), or a pharmaceutically acceptable salt thereof, are in unit dosage form. In further embodiments, the compound of Formula (I) or (Ia), or a pharmaceutically acceptable salt, can be present together with a pharmaceutically acceptable solvent, carrier, excipient, or the like, as described herein.

In some embodiments, the presently disclosed kits comprise one or more containers, including, but not limited to a vial, tube, ampule, bottle and the like, for containing the compound. The one or more containers also can be carried within a suitable carrier, such as a box, carton, tube or the like. Such containers can be made of plastic, glass, laminated paper, metal foil, or other materials suitable for holding medicaments.

In some embodiments, the container can hold a composition that is by itself or when combined with another composition effective for treating or preventing the condition and may have a sterile access port (for example the container may be an intravenous solution bag or a vial having a stopper pierceable by a hypodermic injection needle). Alternatively, or additionally, the article of manufacture may further include a second (or third) container including a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The presently disclosed kits or pharmaceutical systems also can include associated instructions for using the compounds for treating or preventing a neurodegenerative disease, disorder, or condition. In some embodiments, the instructions include one or more of the following: a description of the active compound; a dosage schedule and administration for treating or preventing a neurodegenerative disease, disorder, or condition; precautions; warnings; indications; counter-indications; overdosage information; adverse reactions; animal pharmacology; clinical studies; and references. The instructions can be printed directly on a container (when present), as a label applied to the container, as a separate sheet, pamphlet, card, or folder supplied in or with the container.

G. Chemical Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formula (I) or (Ia) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —C(=O)O— is equivalent to —OC(=O)—; —OC(=O) NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{25}$=S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)R', —C(O)NR', —NR'R", —OR', —SR, and/or —$SO_2$R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH═CH—CH═CH—; —CH═CH—CH$_2$—; —CH$_2$CH$_2$CH$_2$CH$_2$—, —CH$_2$CH═CHCH$_2$—, —CH$_2$C≡CCH$_2$—, —CH$_2$CH$_2$CH(CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxy (—O—CH$_2$—O—); and ethylenedioxy (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

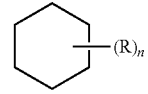

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

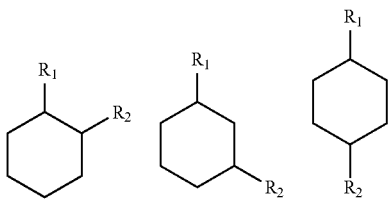

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ($\sim\!\sim\!\sim$) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO$_2$R', —C(O)NR'R", —OC(O)NR'R", —NR"C(O)R', —NR'—C(O)NR"R"', —NR"C(O)OR', —NR—C(NR'R"R"')=NR"", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such groups. R', R", R"' and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R"' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R"', —OC(O)R', —C(O)R', —CO$_2$R', —C(O)NR'R", —OC(O)NR'R", —NR"C(O)R', —NR'—C(O)NR"R"', —NR"C(O)OR', —NR—C(NR'R"R"')=NR"", —NR—C(NR'R")=NR"'—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R", R"' and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R"' and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —S(O)$_2$—, or —S(O)$_2$NR'—. The substituents R, R', R" and R"' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

The term ureido refers to a urea group of the formula —NH—CO—NH$_2$.

Unless otherwise explicitly defined, a "substituent group," as used herein, includes a functional group selected from one or more of the following moieties, which are defined herein:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)— or (S)— or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are encompassed within the scope of the present disclosure.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

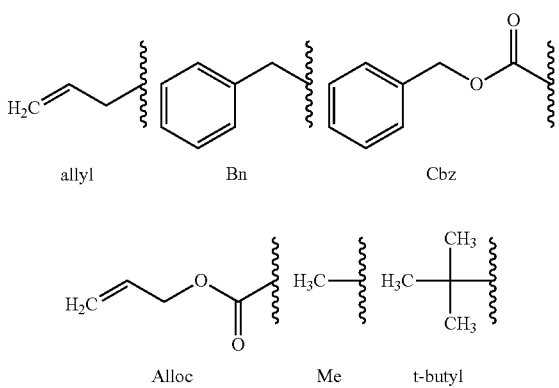

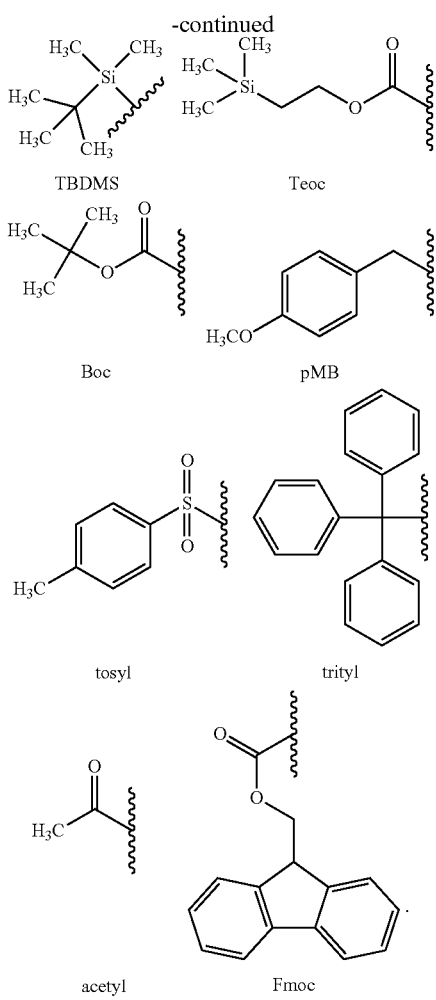

ently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the pres- Example 1

High Content Screening Assay of Small Molecule Libraries

Through a high content screen of small molecule libraries, using a primary screen using cultures of thy-1 immunopanned purified primary murine retinal ganglion cells (RGCs) and various measures of cell viability, including the CellTiter Glow assay, the tyrosine protein kinase inhibitor VX-680 (Tozasertib) was identified as a molecule that could promote the survival of cultured RGCs.

Example 2

RGC Cell Survival Assay with Murine Purified RGCs

The following RGC cell survival assay with murine purified RGCs was used to demonstrate the neuroprotective activity of VX-680, with Sunitinib as a positive control. RGCs were cultured with the indicated drug at the indicated concentration, cultured, and survival was monitored using a calcein AM assay with a Cellomics VTI imager (Thermo Scientific, 100 Technology Drive, Pittsburgh, Pa.) and image analysis software. As shown in FIG. 1, VX-680 (Tozasertib) demonstrates more potent cell survival promoting activity than sunitinib (SUTENT) and also has a wider therapeutic window.

As shown in FIG. 2, a time course of RGC cell survival with murine purified RGCs further demonstrates that the neuroprotective activity of VX-680 exceeds that of sunitinib and a combination of brain derived neurotrophic factor (BDNF) ciliary neurotrophic factor (CNTF), and glial-derived neurotrophic factor (GDNF).

FIG. 3 shows images of murine RGCs cultured in vitro for six days, demonstrating the neuroprotective activity of VX-680. For comparison, data from vehicle and BDNF/CNTF/GDNF also are shown. Data from FIG. 3 at 6 days in vitro (DIV6) are provided in Table 1.

TABLE 1

Murine RGCs Cultured in vitro for Six Days

| Compound | RGC Survival |
|---|---|
| Vehicle | 4.04 ± 0.48 |
| B + C + G | 16.03 ± 2.36 |
| Sunitinib (0.5 μM) | 23.73 ± 1.17 |
| Sunitinib (1 μM) | 26.37 ± 1.61 |
| VX-680 (1 μM) | 49.66 ± 2.27 |
| VX-680 (2 μM) | 60.32 ± 2.47 |

Example 3

Synthesis of Representative Pyrimidine Derivatives

The general synthesis of representative pyrimidine derivatives is provided immediately herein below in Scheme 1.

Scheme 1. General Synthesis of pyrimidine derivatives, JHU-607-612.

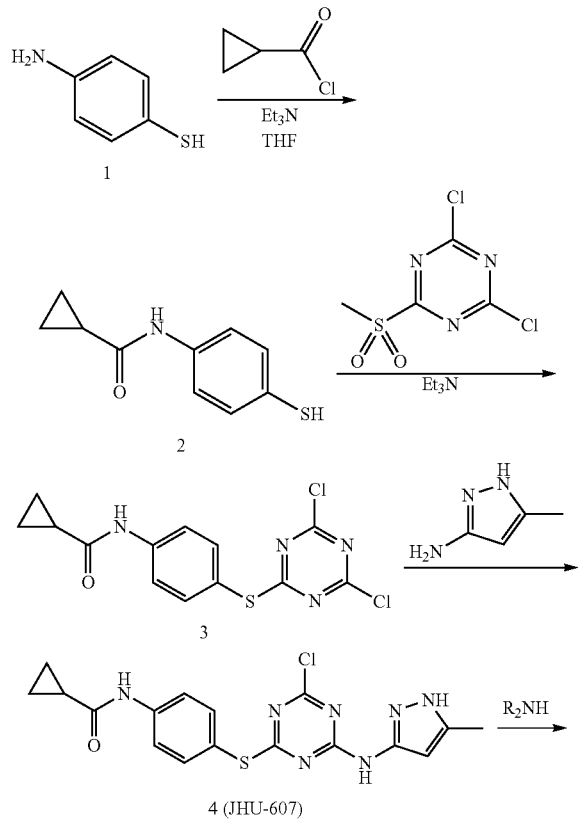

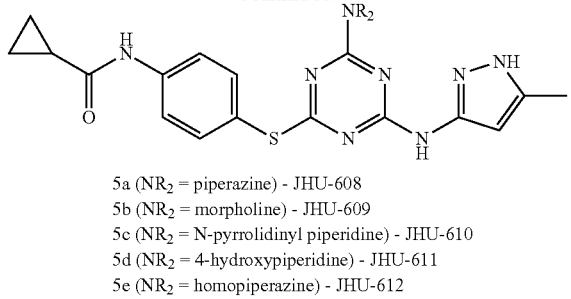

5a ($NR_2$ = piperazine) - JHU-608
5b ($NR_2$ = morpholine) - JHU-609
5c ($NR_2$ = N-pyrrolidinyl piperidine) - JHU-610
5d ($NR_2$ = 4-hydroxypiperidine) - JHU-611
5e ($NR_2$ = homopiperazine) - JHU-612

N-(4-mercaptophenyl)cyclopropanecarboxamide (2). A solution of 4-aminothiophenol, 1 (13.1 g, 105 mmol) was dissolved in THF (100 mL) and cooled to 0° C. Triethyl amine (33 mL, 230 mmol) was added to this solution. A solution of cyclopropylacetyl chloride (21 mL, 230 mmol) was added dropwise over a 1 h. The reaction was warmed to rt overnight. The resulting solids were removed by filtration, washed with THF and discarded. The filtrates were concentrated and the residue was dried in vacuo. The resulting solid was resuspended in EtOH (200 mL) and water (200 mL) and deoxygenated. A solution of 50% NaOH (25 g) was added and the reaction was refluxed at 100° C. for 1 h, cooled to rt, diluted to 1 L with water, decolorized with charcoal, filtered and washed thoroughly with water. The filtrate was acidified with 6 N HCl and the precipitate was collected by filtration, washed with water and dried on high vac to afford 12.0 g of a white powder (59%). LC/MS=194.2 (ES+, M+1).

N-(4-(4,6-dichloro-1,3,5-triazin-2-ylthio)phenyl)cyclopropanecarboxamide (3). A slurry of the dichloropyrimidine (8 g, 35.3 mmol) and thiophenol 2 (7.15 g, 37 mmol) were suspended in acetonitrile (200 mL) and cooled to −20° C. The triethyl amine (5 mL, 35.8 mmol) was added dropwise over 20 min. The reaction was warmed to rt over 2 h and stirred for an additional hour. The reaction was diluted to 500 mL by addition of water and the precipitate that formed was filtered off and washed with water/$CH_3CN$ mixture (1/1, 500 mL). The filtrate was dried under high vac and recrystallized from $CH_3CN$ to afford 5.91 g of a white crystalline solid (49%). LC/MS =341.1 (ES+, M+1).

N-(4-(4-chloro-6-(5-methyl-1H-pyrazol-3-ylamino)-1,3,5-triazin-2-ylthio)phenyl)cyclopropanecarboxamide (4, JHU-607). The dichloropyrimidine 3 (3.41 g, 10 mmoL), 5-methyl-1H-pyrazol-3-amine (1.13 g, 11.6 mmol) and NaI (1.85 g, 12 mmol) were dissolved in anhydrous DMF (20 mL) under $N_2$. The reaction was heated to 90° C. for 20 h, cooled and evaporated to dryness. The residue was suspended in water washed with hexanes, filtered and dried. The crude product was resuspended in $CH_3CN$, brought to reflux, cooled and collected by filtration to afford 2.79 g (70%) of a white solid. LC/MS=402.1 (ES+, M+1).

General Procedure for Synthesis of Amines 5a-5e. The chloropyrimidine 4 (400 mg, 1 mmol), was mixed with each amine (xs, 1-5 eq) in 4 mL of methoxy isopropanol and heated to 110° C. for 1-3 hours. The reaction was then cooled, diluted with water, stirred for 20 min and collected by filtration.

N-(4-(4-(5-methyl-1H-pyrazol-3-ylamino)-6-(piperazin-1-yl)-1,3,5-triazin-2-ylthio)phenyl)cyclopropanecarboxamide (5a, JHU-608). Yield=440 mg (97%); LC/MS=452.3 (ES+, M+1).

N-(4-(4-(5-methyl-1H-pyrazol-3-ylamino)-6-morpholino-1,3,5-triazin-2-ylthio)phenyl)cyclopropanecarboxamide (5b, JHU-609). Yield=440 mg (97%); LC/MS=453.2 (ES+, M+1).

N-(4-(4-(5-methyl-1H-pyrazol-3-ylamino)-6-(4-(pyrrolidin-1-yl)piperidin-1-yl)-1,3,5-triazin-2-ylthio)phenyl)cyclopropanecarboxamide (5c, JHU-610). Yield=500 mg (96%); LC/MS=520.2 (ES+, M+1).

N-(4-(4-(4-hydroxypiperidin-1-yl)-6-(5-methyl-1H-pyrazol-3-ylamino)-1,3,5-triazin-2-ylthio)phenyl)cyclopropanecarboxamide (5d, JHU-611). Yield=450 mg (96%); LC/MS=466.3 (ES+, M+1).

N-(4-(4-(1,4-diazepan-1-yl)-6-(5-methyl-1H-pyrazol-3-ylamino)-1,3,5-triazin-2-ylthio)phenyl)cyclopropanecarboxamide (5e, JHU-612). Yield=460 mg, (99%); LC/MS=466.3 (ES+, M+1).

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

International PCT Patent Application Publication No. WO2010/017541, to Zack et al., for Compositions and Methods for Treatment of Neurodegenerative Disease, published Feb. 11, 2010;

International PCT Patent Application Publication No. WO2011/119777 to Zack et al., for Compositions and Methods for Treatment of Neurodegenerative Disease, published Sep. 29, 2011;

International PCT Patent Application Publication No. WO2011/050192 to Lewcock et al., for Modulation of Axon Degeneration, published Apr. 28, 2011.

International PCT Patent Application Publication No. WO2004/000833 to Charrier et al., for Processes for Preparing Substituted Pyrimidines and Pyrimidine Derivatives as Inhibitors of Protein Kinase, published Dec. 31, 2003;

International PCT Patent Application Publication No. WO2007/056164 to Binch et al., for Aminopyrimidines Useful as Kinase Inhibitors, published May 18, 2007; and International PCT Patent Application Publication No. WO2007/056221 to Binch et al., for Aminopyrimidines Useful as Kinase Inhibitors, published May 18, 2007.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of Formula (Ia):

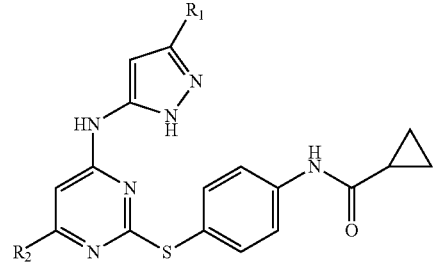

wherein:
R$_1$ is substituted or unsubstituted alkyl;
R$_2$ is a heterocyclic group selected from the group consisting of 4-(pyrrolidin-1-yl)piperidinyl, piperidin-4-ol, and 1,4-diazepanyl; and
pharmaceutically acceptable salts thereof.

2. The compound of claim 1, wherein the compound of Formula (Ia) is selected from the group consisting of:

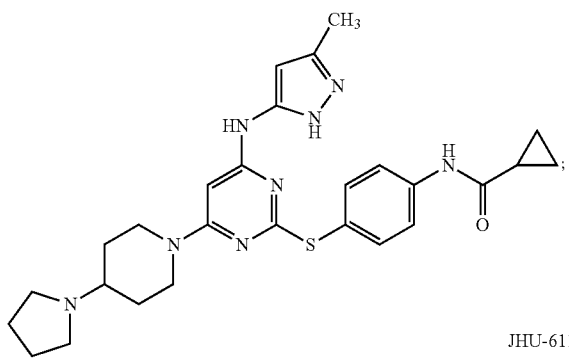

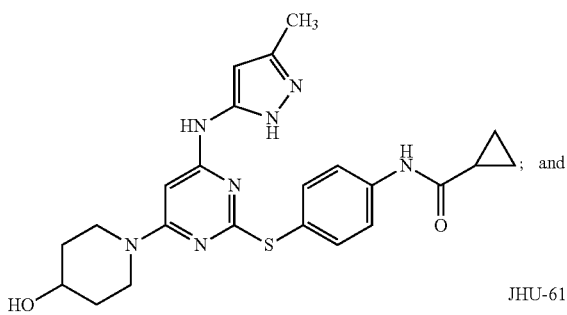

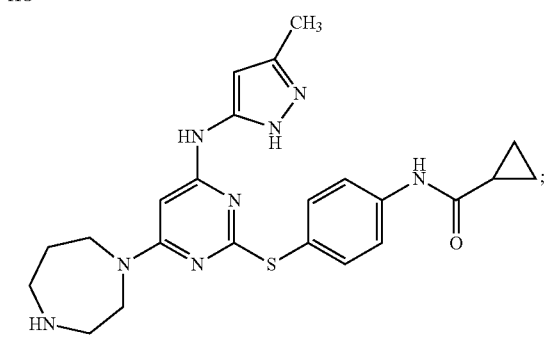

and pharmaceutically acceptable salts thereof.

* * * * *